(12) United States Patent
Akabane et al.

(10) Patent No.: US 10,787,544 B2
(45) Date of Patent: Sep. 29, 2020

(54) SILICONE COMPOUND AND COSMETIC CONTAINING THE SAME

(71) Applicant: SHIN-ETSU CHEMICAL CO., LTD., Tokyo (JP)

(72) Inventors: Emi Akabane, Annaka (JP); Tomoyuki Goto, Annaka (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 27 days.

(21) Appl. No.: 16/315,052

(22) PCT Filed: Apr. 17, 2017

(86) PCT No.: PCT/JP2017/015406
§ 371 (c)(1),
(2) Date: Jan. 3, 2019

(87) PCT Pub. No.: WO2018/012072
PCT Pub. Date: Jan. 18, 2018

(65) Prior Publication Data
US 2019/0211156 A1 Jul. 11, 2019

(30) Foreign Application Priority Data
Jul. 14, 2016 (JP) .................. 2016-139063

(51) Int. Cl.
C08G 77/16 (2006.01)
C08G 77/50 (2006.01)
A61Q 1/06 (2006.01)
A61Q 1/10 (2006.01)
A61Q 1/12 (2006.01)
A61Q 1/14 (2006.01)
A61Q 5/06 (2006.01)
A61Q 17/04 (2006.01)
A61K 8/892 (2006.01)
A61Q 19/04 (2006.01)
A61Q 19/00 (2006.01)

(52) U.S. Cl.
CPC .............. *C08G 77/50* (2013.01); *A61K 8/892* (2013.01); *A61Q 1/06* (2013.01); *A61Q 1/10* (2013.01); *A61Q 1/12* (2013.01); *A61Q 1/14* (2013.01); *A61Q 5/06* (2013.01); *A61Q 17/04* (2013.01); *A61Q 19/00* (2013.01); *A61Q 19/04* (2013.01); *C08G 77/16* (2013.01)

(58) Field of Classification Search
CPC .................. C08G 77/16; C08G 77/50
See application file for complete search history.

(56) References Cited

U.S. PATENT DOCUMENTS 4,698,178 A 10/1987 Huttinger et al.
5,144,054 A 9/1992 Shioya et al.
6,576,623 B1 6/2003 Nakanishi et al.
8,685,376 B2* 4/2014 Czech ................ C11D 1/82
424/70.19
8,715,626 B2* 5/2014 Tamura .................. A61Q 5/12
424/59
9,090,755 B2* 7/2015 Nakanishi .............. A61K 8/891
9,133,309 B2* 9/2015 Iimura ................... A61Q 19/00
9,783,643 B2* 10/2017 Hori ....................... C08G 77/14
2002/0114771 A1 8/2002 Nakanishi
2002/0131947 A1 9/2002 Nakanishi
2004/0091439 A1 5/2004 Kamei et al.
2005/0261133 A1 11/2005 Nakanishi et al.
2010/0004201 A1 1/2010 Matsuo et al.
2010/0266651 A1 10/2010 Czech et al.
2012/0269747 A1* 10/2012 Iimura ................... A61Q 19/00
424/59
2013/0142748 A1* 6/2013 Tamura ................ A61K 8/891
424/70.12
2014/0371330 A1 12/2014 Hayashi et al.

FOREIGN PATENT DOCUMENTS

EP 1213011 A1 6/2002
EP 1213316 A2 6/2002
JP S61-090732 A 5/1986
(Continued)

OTHER PUBLICATIONS

May 16, 2017 Search Report issued in International Patent Application No. PCT/JP2017/015406.
(Continued)

*Primary Examiner* — Margaret G Moore
(74) *Attorney, Agent, or Firm* — Oliff PLC

(57) ABSTRACT

A silicone compound is represented by the formula (1) and has a weight average molecular weight of 500 to 200000. A polyhydric alcohol-modified silicone compound can provide a stable composition (emulsified product, powder dispersion, etc.) having a silicone oil and other oil as a continuous phase.

$$R^1_a R^2_b R^3_c R^4_d SiO_{(4-a-b-c-d)/2} \quad (1)$$

($R^1$ represents an organic group, $R^2$ is a group represented by —Y—O—X (Y represents a divalent hydrocarbon group having 3 to 20 carbons and optionally containing at least one of an ether bond and an ester bond, and X represents a polyhydric alcohol-substituted hydrocarbon group having at least two hydroxyl groups); $R^3$ is a monovalent branched type organosiloxane group represented by the formula (4); and $R^4$ is a monovalent organosiloxane group represented by the formula (5) or the formula (6).)

$$M_o M^R_p D_q D^R_r T_s T^R_t Q_u \quad (4)$$

$$MM^R D_{v1} \quad (5)$$

$$M_w D_{v1} D^R_{v2} T^R_{v3} \quad (6)$$

8 Claims, No Drawings

(56) References Cited

FOREIGN PATENT DOCUMENTS

| | | |
|---|---|---|
| JP | S61-293903 A | 12/1986 |
| JP | S61-293904 A | 12/1986 |
| JP | S62-187406 A | 8/1987 |
| JP | S62-215510 A | 9/1987 |
| JP | S62-216635 A | 9/1987 |
| JP | H04-108795 A | 4/1992 |
| JP | 2001-039819 A | 2/2001 |
| JP | 2002-179798 A | 6/2002 |
| JP | 2004-169015 A | 6/2004 |
| JP | 2005-232088 A | 9/2005 |
| JP | 2005-344076 A | 12/2005 |
| JP | 2006-218472 A | 8/2006 |
| JP | 2010-253472 A | 11/2010 |
| JP | 2013-151657 A | 8/2013 |

OTHER PUBLICATIONS

May 6, 2020 Extended European Search Report issued in European Patent Application No. 17827206.8.

* cited by examiner

SILICONE COMPOUND AND COSMETIC CONTAINING THE SAME

TECHNICAL FIELD

The present invention relates to a novel polyhydric alcohol-modified silicone compound and a cosmetic containing the same.

BACKGROUND ART

In a cosmetic, various oils such as a silicone oil, an ester oil, and a hydrocarbon oil are used, and these are used according to their features and intended use. For example, the silicone oil has features such as excellent usability such as light feeling and being free from stickiness, excellent water-repellent property and high safety. These oils are used singularly or blended in a combination thereof in the cosmetic.

In an emulsion type cosmetic in which an oil and water are blended, a surfactant is generally used. However, when the oil is a silicone oil, it is difficult to obtain an emulsified product having excellent stability even when an emulsifier such as a polyoxyalkylene fatty acid ester type is used. Therefore, a method of using polyoxyalkylene-modified organopolysiloxane (polyether-modified silicone) having excellent compatibility with the silicone oil is proposed (Patent Literatures 1 to 5).

Furthermore, in order to enhance the compatibility with not only the silicone oil but also with other oils, a method of using organopolysiloxane having a long-chain alkyl group and a polyoxyalkylene group, furthermore, a straight chain silicone as an emulsifier is proposed (Patent Literatures 6 and 7).

On the other hand, as a nonionic hydrophilic silicone different from the polyether-modified silicone, a glycerin-modified silicone is known (Patent Literatures 8 to 10). Recently, the glycerin-modified silicone gathers an attention as the surfactant having higher safety because it is considered more excellent in the oxidation stability than the polyether-modified silicone.

Furthermore, the glycerin-modified silicone is also known to have excellent power dispersion stability in a powder dispersion type cosmetic containing powder (Patent Literature 11).

However, in an emulsion composition containing the silicone oil and other oils, there is still a problem in having excellent emulsion stability and securing the temporal stability. In particular, in a cosmetic containing a UV-absorber, it was difficult to secure the stability.

CITATION LIST

Patent Literature

Patent Literature 1: JP S61-293903 A
Patent Literature 2: JP S61-293904 A
Patent Literature 3: JP S62-187406 A
Patent Literature 4: JP S62-215510 A
Patent Literature 5: JP S62-216635 A
Patent Literature 6: JP S61-90732 A
Patent Literature 7: JP 2001-039819 A
Patent Literature 8: JP H04-108795 A
Patent Literature 9: JP 2002-179798 A
Patent Literature 10: JP 2005-344076 A
Patent Literature 11: JP 2006-218472 A

SUMMARY OF INVENTION

Technical Problem

The present invention was carried out in view of the above situations, and intends to provide a polyhydric alcohol-modified silicone compound capable of providing a stable composition (emulsified product, powder dispersion and so on) having the silicone oil and other oils as a continuous phase.

Solution to Problem

In order to solve the above problem, the present invention provides a silicone compound that is represented by the following average composition formula (1) and has a weight average molecular weight of 500 to 200000, $$R^1_a R^2_b R^3_c R^4_d SiO_{(4-a-b-c-d)/2} \quad (1)$$

wherein, "a", "b", "c", and "d" each is $1.0 \le a \le 2.5$, $0.001 \le b \le 1.5$, $0.001 \le c \le 1.5$, and $0 \le d \le 1.0$;

$R^1$ represents an organic group of the same kind or different kinds each other selected from an organic group represented by an alkyl group, a aryl group, an aralkyl group, and a fluorine-substituted alkyl group having 1 to 30 carbon atoms, and a general formula $$-C_lH_{2l}-O-R^5, \quad (2)$$

wherein, $R^5$ represents a hydrogen atom, a hydrocarbon group having 4 to 30 carbons, or an organic group represented by $R^6-(CO)-$, $R^6$ represents a hydrocarbon group having 1 to 30 carbons, and "l" is an integer of $0 \le l \le 15$;

$R^2$ is a group represented by a general formula (3) $-Y-O-X$ wherein, Y represents a divalent hydrocarbon group having 3 to 20 carbons and optionally containing at least one of an ether bond and an ester bond, and X represents a polyhydric alcohol-substituted hydrocarbon group having at least two hydroxyl groups, and optionally contains alkoxy group or ester group;

$R^3$ is a monovalent branched type organosiloxane group represented by the following general formula (4), $$M_o M^R_p D_q D^R_r T_s T^R_t Q_u \quad (4)$$

wherein, $M=R^7_3SiO_{0.5}$, $M^R=R^7_2R^8SiO_{0.5}$, $D=R^7_2SiO$, $D^R=R^7R^8SiO$, $T=R^7SiO_{1.5}$, $T^R=R^8SiO_{1.5}$, $Q=SiO_2$, $R^7$ is an organic group of the same kind or different kinds selected from an alkyl group, an aryl group, an aralkyl group and a fluorine-substituted alkyl group having 1 to 30 carbons, and $R^8$ is an organic group represented by $-C_nH_{2n}-$; "n" represents an integer of $1 \le n \le 5$, "o" is an integer of 1 or larger, "q" and "s" each represents an integer of 0 or larger, "p", "r", "t", and "u" each represents 0 or 1; with the proviso that "s", "t" and "u" are not 0 simultaneously, a sum total of "p", "r" and "t" is 1, and when q=0, "o" represents 2 or larger and a sum total of "s" and "u" is 1 or larger;

$R^4$ is a monovalent organosiloxane group represented by the following general formula (5) or general formula (6), $$MM^R D_{v1} \quad (5)$$

$$M_w D_{v1} D^R_{v2} T^R_{v3} \quad (6)$$

wherein, M, $M^R$, D, $D^R$ and $T^R$ are the same as those described above; v1 is $0 \le v1 \le 500$, v2 and v3 each represents the number of 0 or 1; with the proviso that a sum total of v2 and v3 is 1, and v1 and v3 are not 1 or larger simultaneously; w represents an integer of 2 to 3.

The silicone compound represented by the average composition formula (1) like this has very high affinity with various kinds of oils such as a silicone oil, an ester oil, and a hydrocarbon oil, has excellent emulsification performance and emulsification stability, further may secure excellent emulsification stability even under the presence of the UV-absorber, and is very effective in cosmetic use.

Furthermore, the silicone compound is preferably represented by the following structural formula (1-1),

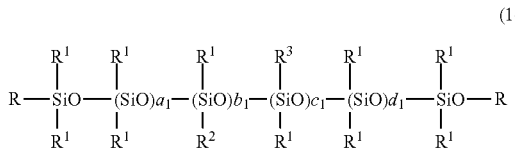
(1-1)

wherein, $R^1$, $R^2$, $R^3$, and $R^4$ are the same as those described above. R may be the same or different from each other and represents a group selected from $R^1$, $R^2$, $R^3$, and $R^4$; $a_1$ is the number in the range of 0 to 1000, $b_1$ is of 0 to 200, $c_1$ is of 0 to 200, and $d_1$ is of 0 to 100; with the proviso that when $b_1=0$, at least one of Rs is $R^2$, and when $c_1=0$, at least one of Rs is $R^3$.

The silicone compound represented by the structural formula (1-1) like this is preferable from the viewpoint of synthesis because a polymerization reaction proceeds readily.

Furthermore, in the silicone compound, the "p" in the general formula (4) is preferably p=1.

A silicone compound in which the "p" is p=1 is preferable from the viewpoint of synthesis because of less steric hindrance when synthesizing.

Furthermore, in the present invention, a cosmetic characterized by containing the silicone compound is provided.

Thus, when the silicone compound of the present invention is blended in the cosmetic as an emulsifying agent and/or a dispersant, excellent temporal stability and excellent usability may be obtained.

Advantageous Effects of Invention

The silicone compound of the present invention has excellent emulsification performance and emulsification stability relative to oils and mixed oils thereof used in general cosmetics such as a silicone oil, an ester oil, and a hydrocarbon oil used in the general cosmetics, further may secure preferable emulsification stability even under the presence of the UV absorber, and still further may secure high temporal stability. Furthermore, the cosmetic containing the silicone compound of the present invention has excellent usability and excellent storage stability.

DESCRIPTION OF EMBODIMENTS

The present inventors studied hard to achieve the above object, and, as a result, found that when a silicone compound that is represented by the following average composition formula (1) and has a weight average molecular weight of 500 to 200000 is used as an emulsifier, the affinity with various kinds of oils such as silicone oils and mixed oils of these is very high, emulsification potential and stability of emulsified products are very excellent, and usage for cosmetics is very effective, and came completion of the present invention.

That is, the present invention provides a silicone compound that is represented by the following average composition formula (1) and has a weight average molecular weight of 500 to 200000, $$R^1_a R^2_b R^3_c R^4_d SiO_{(4-a-b-c-d)/2} \quad (1)$$

wherein, "a", "b", "c", and "d" each is $1.0 \leq a \leq 2.5$, $0.001 \leq b \leq 1.5$, $0.001 \leq c \leq 1.5$, and $0 \leq d \leq 1.0$;

$R^1$ represents an organic group of the same kind or different kinds each other selected from organic groups represented by an alkyl group, an aryl group, an aralkyl group, and a fluorine-substituted alkyl group having 1 to 30 carbon atoms, and a general formula (2) $-C_l H_{21}-O-R^5$, Wherein, $R^5$ represents a hydrogen atom, a hydrocarbon group having 4 to 30 carbons, or an organic group represented by $R^6-(CO)-$; $R^6$ represents a hydrocarbon group having 1 to 30 carbons, and "l" is an integer of $0 \leq l \leq 15$;

$R^2$ is a group represented by a general formula (3) $-Y-O-X$ wherein, Y represents a divalent hydrocarbon group having 3 to 20 carbons and optionally containing at least one of an ether bond and an ester bond, and X represents a polyhydric alcohol-substituted hydrocarbon group having at least two hydroxyl groups and optionally contains an alkoxy group or an ester group;

$R^3$ is a monovalent branched organosiloxane group represented by the following general formula (4), $$M_o M^R_p D_q D^R_r T_s T^R_t Q_u \quad (4)$$

wherein, $M=R^7_3 SiO_{0.5}$, $M^R=R^7_2 R^8 SiO_{0.5}$, $D=R^7_2 SiO$, $D^R=R^7 R^8 SiO$, $T=R^7 SiO_{1.5}$, $T^R=R^8 SiO_{1.5}$, $Q=SiO_2$, $R^7$ is an organic group of the same kind or different kinds selected from an alkyl group, an aryl group, an aralkyl group and a fluorine-substituted alkyl group having 1 to 30 carbons, and $R^8$ is an organic group represented by $-C_n H_{2n}-$; "n" represents an integer of $1 \leq n \leq 5$, "o" is an integer of 1 or larger, "q" and "s" each represents an integer of 0 or larger, "p", "r", "t", and "u" each represents 0 or 1; with the proviso that "s", "t" and "u" are not 0 simultaneously, a sum total of "p", "r" and "t" is 1, and when q=0, "o" represents 2 or larger and a sum total of "s" and "u" is 1 or larger;

$R^4$ is a monovalent organosiloxane group represented by the following general formula (5) or general formula (6), $$MM^R D_{v1} \quad (5)$$

$$M_w D_{v1} D^R_{v2} T^R_{v3} \quad (6)$$

wherein, M, $M^R$, D, $D^R$ and $T^R$ are the same as those described above; v1 is $0 \leq v1 \leq 500$, v2 and v3 each represents the number of 0 or 1; with the proviso that a sum total of v2 and v3 is 1, and v1 and v3 are not 1 or larger simultaneously; w represents an integer of 2 to 3.

The $R^1$ in the formula (1) represents an organic group of the same kind or different kinds each other selected from organic groups represented by an alkyl group, an aryl group, an aralkyl group, and a fluorine-substituted alkyl group having 1 to 30 carbon atoms, and a general formula $$-C_l H_{21}-O-R^5. \quad (2)$$

Specific examples of the alkyl group of the $R^1$ include a methyl group, an ethyl group, a propyl group, a butyl group, a pentyl group, a hexyl group, a heptyl group, an octyl group, a nonyl group, a decyl group, a cyclopentyl group and a cyclohexyl group. Specific examples of the aryl group include a phenyl group and a tolyl group. Specific examples of the aralkyl group include a benzyl group and a phenethyl group. Specific examples of the fluorine-substituted alkyl group include a trifluoropropyl group and a heptadecafluoro decyl group.

Furthermore, the $R^1$ may be the same kind or different kinds of an alkoxy group, an ester group, an alkenyl ether residual group, or an alkenyl ester residual group selected from organic groups represented by a general formula (2) $-C_l H_{21}-O-R^5$; with the proviso that the $R^5$ in the formula (2) represents a hydrogen atom, a hydrocarbon group having 4 to 30 carbons, or an organic group represented by $R^6$—(CO)—; the $R^6$ is a hydrocarbon group having 1 to 30 carbon atoms, and "l" is an integer of $0 \leq l \leq 15$.

Examples of hydrocarbon groups having 4 to 30 carbons of the $R^5$ include a butyl group, a pentyl group, a hexyl group, a heptyl group, an octyl group, a nonyl group, a decyl group, a cyclopentyl group, a cyclohexyl group, a phenyl group, a tolyl group, a benzyl group and a phenethyl group, and examples of hydrocarbon groups having 1 to 30 carbons of the $R^6$ include a methyl group, an ethyl group, a propyl group, a butyl group, a pentyl group, a hexyl group, a heptyl group, an octyl group, a nonyl group, a decyl group, a cyclopentyl group, a cyclohexyl group, a phenyl group, a tolyl group, a benzyl group and a phenethyl group.

For example, when the l is 0, a silanol group (—OH) or an alkoxy group having 4 to 30 carbon atoms is obtained, and specific examples thereof include from lower alkoxy groups such as a butoxy group to higher alkoxy groups such as an oleiloxy group, and a stearoxy group. Alternatively, ester groups of acetic acid, lactic acid, butyric acid, oleic acid, stearic acid, or behenic acid may be used.

Furthermore, when the l is 1 or larger, the l is particularly preferable to be 3, 5 or 11. The $R^1$ in this case is an aryl ether residue, a pentenyl ether residue, or an undecenyl ether residue, and depending on the substituent of the $R^5$, for example, an aryl stearyl ether residue, a propenyl behenyl ether residue or an undecenyl oleyl ether residue is exemplified.

Here, when the "l" becomes larger than 15, odor of oil becomes stronger. Therefore, the "l" is 15 or smaller, furthermore, preferable to be 3 to 5 from the viewpoint of hydrolysis resistance.

Furthermore, in the present invention, it is preferable for 50% or higher of an entire $R^1$ in the formula (1) to be a methyl group, and more preferable for 70% or larger thereof to be the methyl group, and there may be a case where the methyl group is 100%.

The $R^2$ in the formula (1) is represented by a general formula (3) —Y—O—X, here, the Y represents a divalent hydrocarbon group of 3 to 20 carbons having optionally at least one of an ether bond and an ester bond, and —(CH$_2$)$_3$—, —CH$_2$CH(CH$_3$)CH$_2$—, —(CH$_2$)$_4$—, —(CH$_2$)$_5$—, —(CH$_2$)$_6$—, —(CH$_2$)$_7$—, —(CH$_2$)$_8$—, —(CH$_2$)$_2$—CH(CH$_2$CH$_2$CH$_3$)—, —CH$_2$—CH(CH$_2$CH$_3$)—, —(CH$_2$)$_3$—O—(CH$_2$)$_2$—, —(CH$_2$)$_3$—O—(CH$_2$)$_2$—O—(CH$_2$)$_2$—, —(CH$_2$)$_3$—O—CH$_2$CH(CH$_3$)—, and —CH$_2$—CH(CH$_3$)—COO(CH$_2$)$_2$— may be exemplified. The X is a polyhydric alcohol-substituted hydrocarbon group having at least two hydroxyl groups, may contain an alkoxy group or an ester group, preferably a hydrocarbon group having at least two hydroxyl groups derived from one selected from (poly)glycerin and a sugar derivative, and more preferably a polyglycerin derivative.

As examples of the $R^2$ in the formula (1) when the X is the polyglycerin derivative, groups of the formula below are cited, the Y in the formula below is the same as the Y in a formula (3), "g" and "h" in the formula are integers of 1 to 20. Furthermore, a part of the hydroxyl groups in the following compounds may be substituted with an alkoxy group or an ester group.

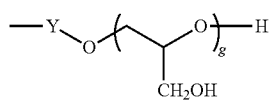

(2-1)

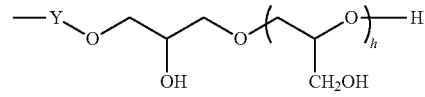

(2-2)

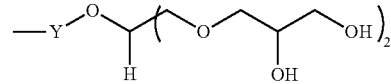

(2-3)

The $R^3$ in the above formula (1) is a monovalent branched organosiloxane group represented by the following general formula (4), $$M_o M^R{}_p D_q D^R{}_r T_s T^R{}_t Q_u \qquad (4)$$

wherein, $M=R^7{}_3SiO_{0.5}$, $M^R=R^7{}_2R^8SiO_{0.5}$, $D=R^7{}_2SiO$, $D^R=R^7R^8SiO$, $T=R^7SiO_{1.5}$, $T^R=R^8SiO_{1.5}$, and $Q=SiO_2$ are represented.

The $R^7$ is an organic group of the same kind or different kinds selected from organic groups represented by an alkyl group, an aryl group, an aralkyl group and a fluorine-substituted alkyl group having 1 to 30 carbons, and specific examples include: alkyl groups such as a methyl group, an ethyl group, a propyl group, a butyl group, a pentyl group, a hexyl group, a heptyl group, an octyl group, a nonyl group, a decyl group, a cyclopentyl group and a cyclohexyl group; aryl groups such as a phenyl group and a tolyl group; aralkyl groups such as a benzyl group and a phenethyl group; and fluorine-substituted alkyl groups such as a trifluoropropyl group and a heptadecafluorodecyl group.

The $R^7$ is preferable that methyl groups are 50% or larger of an entirety and more preferably 70% or larger thereof, and the methyl groups may be 100%.

The $R^8$ is an organic group represented by —$C_nH_{2n}$—; the "n" is an integer of 1 to 5, and preferably n=2.

The "o" is an integer of 1 or larger, preferably an integer of 1 to 200, and more preferably an integer of 1 to 100. The "q" is an integer of 0 or larger, preferably an integer of 0 to 500, and more preferably an integer of 1 to 200. The "s" is an integer of 0 or larger, preferably an integer of 0 to 100, and more preferably an integer of 1 to 50, the "u" is 0 or 1, and preferably 1. The "p", "r" and "t" each is 0 or 1, although a sum total of "p", "r" and "t" is 1, p=1 that is slight in the steric hindrance is preferable from the viewpoint of synthesis. Furthermore, "s", "t" and "u" are not 0 simultaneously, and when q=0, the "o" is 2 or larger and a sum total of "s" and "u" has to be 1 or larger.

The $R^4$ in the formula (1) is a monovalent organosiloxane group represented by the following general formula (5) or general formula (6).

$$MM^R D_{v1} \qquad (5)$$

$$M_w D_{v1} D^R{}_{v2} T^R{}_{v3} \qquad (6)$$

Here, M, $M^R$, D, $D^R$ and $T^R$ are the same as those described above; v1 is 0 to 500, and preferably 3 to 50. When the v1 is larger than 500, there may occur a problem such as deterioration of the reactivity when synthesizing. The v2 and v3 each is the number of 0 or 1, and a sum total of v2 and v3 is 1. Furthermore, the v1 and v3 do not become 1 or larger simultaneously. The "w" is an integer of 2 to 3.

The "a" is 1.0 to 2.5 and preferably 1.2 to 2.3. When the "a" is smaller than 1.0, since the compatibility with the oil is poor, it is difficult to obtain a stable emulsified product, and when the "a" is larger than 2.5, since the hydrophilicity becomes poor, it is also difficult to obtain a stable emulsified product. The "b" is 0.001 to 1.5 and preferably 0.05 to 1.0. When the "b" is smaller than 0.001, since the hydrophilicity becomes poor, it is difficult to obtain a stable emulsified product, and when larger than 1.5, since the hydrophilicity becomes too large, it is difficult to obtain a stable emulsified product. The "c" is 0.001 to 1.5 and preferably 0.05 to 1.0. When the "c" is smaller than 0.001, since the compatibility with the silicone oil is poor, it is difficult to obtain a stable emulsified product, and when larger than 1.5, since the hydrophilicity becomes poor, it is also difficult to obtain a stable emulsified product. The "d" is 0 to 1.0 and preferably 0 to 0.5. When the "d" is larger than 1.0, since the hydrophilicity becomes poor, it is difficult to obtain a stable emulsified product.

As the emulsifier, a weight average molecular weight of a silicone compound represented by the formula (1) is 500 to 200000 and preferably 1000 to 100000. When the molecular weight is smaller than 500, a stable emulsified product is difficult to obtain, and when larger than 200000, handling is poor, and excellent usability becomes difficult to obtain. Here, the weight average molecular weight may be measured by a gel permeation chromatography (GPC) analysis in terms of polystyrene (the same hereinafter).

Furthermore, the silicone compound represented by the formula (1), which is represented by the following structural formula (1-1), is preferable because of easy synthesis,

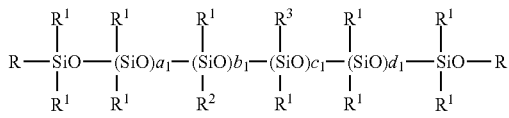

(1-1)

wherein, $R^1$, $R^2$, $R^3$, and $R^4$ are the same as those described above; R may be the same or different from each other and represents a group selected from $R^1$, $R^2$, $R^3$, and $R^4$; $a_1$ is the number in the range of 0 to 1000, $b_1$ is the number in the range of 0 to 200, $c_1$ is the number in the range of 0 to 200, and $d_1$ is the number in the range of 0 to 100; with the proviso that when $b_1=0$, at least one of Rs is $R^2$, and when $c_1=0$, at least one of Rs is $R^3$.

The silicone compound represented by the formula (1) of the present invention may be readily synthesized by performing an additional reaction of organohydrogenpolysiloxane, a polyhydric alcohol-substituted hydrocarbon derivative having one reactive unsaturated group in one molecule, and a silicone compound having a $C_nH_{(2n-1)}$-group, depending on the case, further a terminal alkene compound, under the presence of a platinum catalyst or a rhodium catalyst. The "n" is the same as that described above.

Here, the organohydrogenpolysiloxane may be any one of a straight chain, a branched chain, or a ring type. However, from the viewpoint of smoothly forwarding a polymerization reaction, a straight chain type, mainly a straight chain type shown by the following formula (1-2) is preferred.

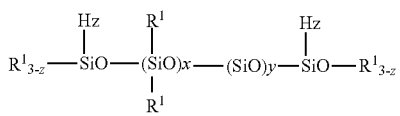

(1-2)

In the formula (1-2), $R^1$ represents the above group, and "x" is $0 \leq x \leq 1000$, preferably $0 \leq x \leq 300$, and more preferably $0 \leq x \leq 100$. When "x" is 1000 or smaller, there is no fear of degradation of the reactivity, and there is no fear of degradation of usability. "y" is $0 \leq y \leq 300$, preferably $1 \leq y \leq 100$, and more preferably $2 \leq y \leq 50$. When the "y" is 300 or smaller, there is no fear such that the hydrophilicity becomes too high to be difficult to obtain a stable emulsified product. Furthermore, the reaction is easily completed. "z" is 0 to 2 and is preferably 0 to 1.

As the polyhydric alcohol-substituted hydrocarbon derivative having one reactive unsaturated group in a molecule, a derivative having a reactive unsaturated group represented by $C_mH_{(2m-1)}$-group at a molecular chain terminal, here "m" is an integer of 1 to 15, preferably 3 to 5, and represented by $C_3H_5$—O—X (X is the same as the above) is most preferable. Furthermore, these may be synthesized according to well-known methods.

As a silicone compound having a $C_nH_{(2n-1)}$-group, a silicone compound represented by the following general formula (7), and, as needs arise, a silicone compound represented by the following general formula (8) or general formula (9) may be used.

$$M_o M^{R'}_p D_q D^{R'}_r T_s T^{R'}_t Q_u \qquad (7)$$

wherein, $M=R^7_3SiO_{0.5}$, $M^{R'}=R^7_2R^{15}SiO_{0.5}$, $D=R^7_2SiO$, $D^{R'}=R^7R^{15}SiO$, $T=R^7SiO_{1.5}$, $T^{R'}=R^{15}SiO_{1.5}$, $Q=SiO_2$, and $R^{15}$ is an organic group represented by $C_nH_{(2n-1)}$. The $R^7$, "n", "o", "p", "q", "r", "s", "t" and "u" are as described above. Additionally, when p=1, due to less steric hindrance, high reactivity is obtained.

The silicone compound represented by the general formula (7) like this has an organic group represented by one $C_nH_{(2n-1)}$- and has a branched structure having high functionality ("s", "t" and "u" are not 0 simultaneously, a sum total of "p", "r" and "t" is 1, when q=0, "o" is 2 or larger and a sum total of "s" and "u" is 1 or larger) The compound like this has very excellent reactivity and suitable as a raw material of the silicone compound of the present invention.

$$MM^{R'}D_{v1} \qquad (8)$$

$$M_w D_{v1} D^{R'}_{v2} T^{R'}_{v3} \qquad (9)$$

wherein, $M=R^7_3SiO_{0.5}$, $M^{R'}=R^7_2R^{15}SiO_{0.5}$, $D=R^7_2SiO$, $D^{R'}=R^7R^{15}SiO$, $T^{R'}=R^{15}SiO_{1.5}$ and $R^{15}$ is an organic group represented by $C_nH_{(2n-1)}$; $R^7$, v1, v2 and v3 each is as shown above. Additionally, when v1 in the formula is larger than 500, there may occur a problem such that the reactivity with the organohydrogensiloxane is degraded.

When a silicone compound obtained by adding a straight chain or low molecular weight branched organosiloxane represented by the general formula (8) or general formula (9) is contained in the cosmetic, more refreshing and light feeling may be obtained.

As the terminal alkene compound, terminal alkene compounds having 6 to 30 carbons are preferable, for example, 1-dodecene or the like is cited. When a silicone compound obtained by adding a long chain terminal alkene compound such as 1-dodecene is used, the affinity with oils used in general cosmetics such as silicone oil, ester oil, hydrocarbon oil becomes higher to be able to obtain silicone compounds having excellent emulsifying capacity.

A mixing ratio of the organohydrogenpolysiloxane and a sum total of the polyhydric-substituted hydrocarbon derivative having one reactive unsaturated group in one molecule, the silicone compound having the $C_nH_{(2n-1)}$-group, and the terminal alkene compound is preferable to be 0.5 to 2.0, particularly preferable to be 0.8 to 1.2 by a molar ratio of the terminal unsaturated groups to 1 mole of SiH groups.

Furthermore, the additional reaction is desirably carried out under the presence of a platinum catalyst or rhodium catalyst, specifically, a catalyst such as chloroplatinic acid, alcohol-modified chloroplatinic acid, or chloroplatinic acid-vinyl siloxane complex may be preferably used. Although a used amount of the catalyst may be set to a catalytic amount, in particular, a platinum or rhodium amount relative to a total mass of raw materials used is 0.01 to 50 ppm, and preferably 0.1 to 20 ppm. When the amount of the catalyst is within the above range, the additional reaction proceeds without making the reaction speed slower to be economically preferable.

The additional reaction may be performed in an organic solvent as needs arise. Examples of the organic solvent include: aliphatic alcohols such as methanol, ethanol, 2-propanol, and butanol; aromatic hydrocarbons such as toluene and xylene; aliphatic or alicyclic hydrocarbons such as n-pentane, n-hexane and cyclohexane; and halogenated hydrocarbons such as dichloromethane, chloroform, and carbon tetrachloride. In particular, for cosmetic use, ethanol and 2-propanol (isopropyl alcohol) are suitable. Although the condition of the additional reaction is not particularly limited, a reaction is preferably performed for 1 to 10 hours under reflux. An amount of the solvent is not particularly limited and may be appropriately adjusted.

Furthermore, a residual SiH group may be hydrolyzed, as needs arise, by using an alkaline substance. A treatment may be performed with only water, however, in order to control the reaction constant, the alkaline substance is preferably added and performed. An added amount of the alkaline substance to be added when hydrolyzing the residual SiH group is 0.0001 to 10 pts·mass, and preferably 0.001 to 10 pts·mass relative to 100 pts·mass of the organohydrogenpolysiloxane to be used. When the added amount is 0.0001 or larger, a sufficient hydrolysis effect is obtained, and when the added amount is 10 pts·mass or smaller, there is no fear of occurrence of unfavorable reaction such as breakage of siloxane chain. Furthermore, the alkaline substance may be added as it is, however, by considering a contact rate with the organohydrogenpolysiloxane, it is preferable to add as an aqueous solution of 1 to 50 mass %.

As a treatment condition after addition of the alkaline substance, it is preferable to heat to 10 to 80° C., and particularly preferable to heat to 10 to 50° C. Furthermore, in order to perform a neutralization reaction after the end of hydrolysis, an acidic substance may be added. The acidic substance may be added as it is, it may be added as an aqueous solution of 1 to 50 mass %. The added amount may be adjusted such that equivalents of functional groups of the alkaline substance and the acidic substance are preferably 1/0.1 to 0.1/1, particularly preferably, 1/0.3 to 0.3/1, and pH after neutralization is 5 to 8.

Furthermore, as needs arise, a purification treatment with an acidic substance may be applied. Although the treatment may be performed with only water, in order to control a reaction uniformly, it is preferred to perform by adding the acidic substance. An added amount of the acidic substance is 0.0000001 to 10 pts·mass and preferably 0.000001 to 1 pt·mass relative to 100 pts·mass of the silicone compound represented by the average composition formula (1). In the case of 0.0000001 pt·mass or larger, a deodorant effect may be sufficiently obtained, and in the case of 10 pts·mass or smaller, there is preferably no fear of deposition of a large amount of neutralized salt in a composition after the treatment. Furthermore, although these acidic substances may be added as they are, it is preferable to add as an aqueous solution of 1 to 50% from the viewpoint of a contact efficiency with a treatment liquid.

As a treatment condition after addition of the acidic substance, heating may not be applied, but it is applied at 20 to 150° C., particularly preferably at 50 to 100° C. In the case of performing a neutralization reaction, when the alkaline substance is used, it may be added as it is, but it is preferable to add as an aqueous solution of 1 to 50 mass %. Furthermore, an added amount is adjusted such that equivalents of functional groups of the acidic substance and the alkaline substance are 1/0.1 to 0.1/1, preferably 1/0.3 to 0.3/1, and the pH after neutralization becomes 5 to 8. A treatment condition after addition of the alkaline neutralizer is 20 to 150° C., preferably 20 to 80° C.

Specific examples of the alkaline substance include sodium carbonate, sodium hydrogen carbonate, sodium hydroxide, potassium hydroxide, disodium hydrogen phosphate, and sodium acetate, however, sodium carbonate, sodium hydrogen carbonate and sodium hydroxide are particularly preferable. As the acidic substance, inorganic acids and organic acids and salts thereof may be used. Examples of the inorganic acid include hydrochloric acid, sulfuric acid, nitric acid, carbonic acid, and phosphoric acid, and examples of the organic acid include formic acid, acetic acid, carboxylic acid such as trifluoroacetate, sulfonic acid, sulfinic acid, phenolic acid, and primary and secondary nitro compounds. From the viewpoint of treatment efficiency, hydrochloric acid that is a strong acid and trifluoroacetic acid are preferably used; with the proviso that the neutralization reaction is preferably selected from a combination in which a salt generated by neutralization has a buffering agent effect of pH, and by doing like this, not only the odor is reduced but also a pH stabilizing effect of the composition may be obtained. A specific method of the treatment method is performed according to a method described in Patent Literature 7.

A branched organosiloxane having the $C_nH_{(2n-1)}$-group represented by the above general formula (7) that becomes a monovalent branched organosiloxane group represented by the general formula (4) after the addition reaction may be obtained by reacting organosiloxane having only one silanol group in a molecule with an organic chlorosilane compound under the presence of hydrochloric acid. Specifically, it may be obtained by a "step 1" and a "step 2" shown below, or by repeating the "step 1" and the "step 2".

The "step 1" is a step of obtaining organosiloxane having only one silanol group in a molecule by reacting an organohydrogensiloxane represented by the following general formula (10), $$M_{o-1}M^H_{p-1}D_{q-1}D^H_{r-1}T_{s-1}T^H_{t-1}Q_{u-1} \qquad (10)$$

($M=R^7_3SiO_{0.5}$, $M^H=R^7_2HSiO_{0.5}$, $D=R^7_2SiO$, $D^H=HR^7SiO$, $T=R^7SiO_{1.5}$, $T^H=HSiO_{1.5}$, $Q=SiO_2$, and $R^7$ is the same as that described above, o–1 is an integer of 1 or larger, q–1 and s–1 each is an integer of 0 or larger, p–1, r–1, t–1, and u–1 each is 0 or 1; with the proviso that s–1, t–1 and u–1 are not 0 simultaneously, a sum total of p–1, r–1 and t–1 is 1, when q–1 is 0, o–1 is 2 or larger and a sum total of s–1 and u–1 is 1 or larger) with water under the presence of a catalyst.

Although a production method of an organohydrogensiloxane represented by the above general formula (10) is already a well-known technology, ones due to a hydrolytic condensation of an organic silicon compound having a SiH group and an organic silicone compound having an alkyl group or a living polymerization are cited, as needs arise, a purification treatment such as distillation may be applied. Furthermore, a commercially available product may be purchased.

As a catalyst to be used, transition metal catalysts or Lewis acid catalysts may be used. Examples of the transition metal catalyst include ruthenium catalysts, rhodium catalysts, palladium catalysts, iridium catalysts, platinum catalysts, and gold catalysts, and the palladium catalyst is particularly preferable. Furthermore, examples of the Lewis catalyst include aluminum chloride, aluminum sulfate, stannic chloride, stannic chloride sulfate, ferric chloride, boron trifluoride, and pentafluorophenyl boron, among these, the pentafluorophenyl boron is particularly preferable.

In the "step 1", a solvent may be used as needs arise. As the solvent, although there is no particular restriction as long as it is nonreactive with the organohydrogensiloxane represented by the general formula (10) that is a raw material and the catalyst, specific examples include: aliphatic hydrocarbon-based solvents such as pentane, hexane, heptane and decane; aromatic hydrocarbon-based solvents such as benzene, toluene, and xylene; and ether-based solvents such as diethyl ether, tetrahydrofuran, and 1, 4-dioxane. An amount of the solvent is not particularly restricted and may be appropriately adjusted.

In the "step 1", when the organosiloxane having only one silanol group in the molecule is produced, although a blending ratio of the organohydrogensiloxane of the above general formula (10) and the catalyst is not particularly restricted, from the viewpoint of reactivity and productivity, it is desirable to make the catalyst react in the range of 0.000001 to 0.1 mole, particularly 0.000001 to 0.01 mole relative to 1 mole of the organohydrogensiloxane of the general formula (10). In the case of 0.000001 mole or larger, since a reaction speed does not become slow, a reaction time becomes shorter, and in the case of 0.1 mole or smaller, preferably, there is no fear that the organosiloxane having only one silanol group in the molecule that is a reaction product is made higher polymer due to a redistribution reaction to result in decreasing a yield.

Furthermore, when the organosiloxane having only one silanol group in the molecule is produced, although a blending ratio of the organohydrogensiloxane of the general formula (10) and water is not particularly restricted, from the viewpoint of the reactivity and productivity, it is desirable to make react water in the range of 1 to 5 mole, particularly 1.05 to 3.0 mole relative to 1 mole of the organohydrogensiloxane of the general formula (10). In the case of 1 mole or larger, the reaction proceeds completely to result in a sufficient yield, and in the case of 5 mole or smaller, while improving the yield, also a pot yield may be made sufficient.

In the "step 1", it is desirable to make react at a temperature in the range of 1° C. to 70° C., in particular of 5° C. to 40° C. A reaction time is set to 30 minutes to 10 hours depending on a proceeding degree of the reaction but is particularly preferable to make react in the range of 1 hour to 8 hours. Furthermore, as needs arise, a purification treatment such as distillation may be performed, and under normal pressure or reduced pressure, a conventional method may be performed.

The "step 2" is a step where the organosiloxane having only one silanol group in the molecule obtained in the "step 1" is reacted with an organic chlorosilane compound under the presence of a base.

The base that is a raw material necessary in the "step 2" is not particularly restricted. Specific examples thereof include sodium carbonate and amine-based bases such as pyridine, triethylamine, ammonia, methylamine, ethylamine, dimethylamine, N-hexylamine, N-ethyldiisopropylamine, imidazole, and N-methylimidazole.

Furthermore, although as the organic chlorosilane compound of a raw material, there is no particular restriction, when an obtained compound is used as the silicone compound represented by the general formula (7), an organic chlorosilane compound having a $C_nH_{(2n-1)}$-group is preferable, and, in particular, dimethyl vinyl chlorosilane is commercially available and can be readily obtained. Furthermore, when the obtained compound is used as the general formula (10) in the "step 1" to obtain a polymer having a highly branched structure, dimethylchlorosilane, methyldichlorosilane and trichlorosilane are commercially available and may be readily obtained.

In the "step 2", as needs arise, a solvent may be used. As the solvent, there is no particular restriction as long as the solvent is nonreactive with the organohydrogensiloxane represented by the above general formula (10) that is a raw material, the base, and the organic chlorosilane compound. Specific examples thereof include aliphatic hydrocarbon-based solvents such as pentane, hexane, heptane and decane; aromatic hydrocarbon-based solvents such as benzene, toluene, and xylene; and ether-based solvents such as diethyl ether, tetrahydrofuran, and 1, 4-dioxane. An amount of the solvent is not particularly restricted and may be appropriately adjusted.

Furthermore, when the branched organopolysiloxane having the $C_nH_{(2n-1)}$-group of the general formula (7) is produced, a blending ratio of the organosiloxane having only one silanol group in the molecule obtained in the "step 1" and the organic chlorosilane compound is not particularly restricted. However, from the viewpoint of the reactivity and productivity, it is desirable to make react Si—Cl groups in the organic chlorosilane compound in the range of 0.01 to 2.0 mole, in particular, 0.4 to 1.2 mole relative to 1 mole of the organosiloxane obtained in the "step 1". In the case of 0.01 mole or larger, a yield of monofunctional branched organosiloxane compound becomes sufficient, and in the case of 2.0 mole or smaller, while improving the yield, a pot yield is also made sufficient.

Furthermore, in the "step 2", although a blending ratio of the organic chlorosilane compound and the base is not particularly restricted, from the viewpoint of the reactivity and productivity, it is desirable to make the base react in the range of 0.1 to 6.0 mole, in particular, of 0.4 to 3.0 mole relative to 1 mole of Si—Cl groups in the organic chlorosilane compound. In the case of 0.1 mole or larger, a reaction speed does not become slow to result in a short reaction time, and in the case of 6.0 mole or smaller, the monofunctional branched organosiloxane compound that is a reaction product is readily isolated to result in sufficient yield.

A reaction temperature of the "step 2" is 1° C. to 80° C., particularly preferably 5° C. to 40° C. The reaction is preferably performed in the reaction time in the range of 30 minutes to 20 hours, in particular 1 hour to 10 hours.

In the "step 2", when amines such as ammonia are used as the base, the organic chlorosilane is previously reacted and may go through organic silazane. According to this method, a salt may be suppressed from being by-produced. Furthermore, it is desirable to set a reaction temperature at this time in the range of 1° C. to 80° C., preferably 5° C. to 50° C. The reaction is preferably performed in the reaction time in the range of 30 minutes to 20 hours, in particular 1 hour to 10 hours.

Furthermore, in the present production method, as needs arise, a purification treatment such as distillation may be performed, and under normal pressure or reduced pressure, a conventional method may be performed.

The silicone compounds of the present invention may be used in various applications, and are particularly preferable as raw materials for all cosmetics externally used on a skin or hairs. In this case, a blending amount of the silicone compound represented by the average composition formula (1) is, though different depending on kinds and formulations of the cosmetics, preferably roughly in the range of 0.1 to 50 mass % of an entirety of the cosmetic.

The cosmetic of the present invention preferably contains a silicone oil in addition to the silicone compound represented by the average composition formula (1). Specific examples of the silicone oil preferably include dimethyl polysiloxane, methyl phenyl polysiloxane, methyl trimethicone, phenyl trimethicone, decamethylcyclopentanesiloxane, dodecamethylcyclohexasiloxane, octamethyl trisiloxane, decamethyltetrasiloxane, dodecamethylpentasiloxane, heptamethylethyltrisiloxane, caprylyl methicone, and tetrakistrimethylsiloxysilane. Since the silicone compound represented by the average composition formula (1) has excellent emulsifying property particularly to the silicone oil, when the cosmetic of the present invention contains the silicone oil, stability of emulsion cosmetics is increased. Furthermore, cosmetics free from stickiness may be obtained. These silicone oils may be used singularly or in a combination of two or more kinds. As a blending amount of the silicone oil, 2 to 40 mass % of an entire cosmetic is preferable, and it is particularly preferably blended so as to be 5 to 20 mass %. When in the range of 2 to 40 mass %, preferably there is no fear of damaging the emulsion stability.

The cosmetic of the present invention preferably further contains a non-emulsifiable silicone elastomer. The non-emulsifiable silicone elastomer preferably swells by containing a low viscosity silicone more than self-weight relative to the low viscosity silicone having dynamic viscosity due to an Ostwald viscometer of 0.65 to 10.0 mm$^2$/s (25° C.). Furthermore, the non-emulsifiable silicone elastomer preferably has a crosslinking structure formed by a reaction of a crosslinking agent having two or more vinyl reactive sites in a molecule and a hydrogen atom directly bonded to a silicon atom. Furthermore, the non-emulsifiable silicone elastomer preferably contains a moiety of at least one kind selected from the group consisting of an alkyl moiety, an alkenyl moiety, an aryl moiety, and a fluoroalkyl moiety. A blending amount in the case where the non-emulsifying silicone elastomer is used is preferably 0.1 to 30 mass %, and particularly preferably 1 to 10 mass % relative to a total amount of the cosmetic.

As the non-emulsifiable silicone elastomer, specifically, dimethicone/vinyl dimethicone crosspolymer of (KSG-15, KSG-16) manufactured by Shin-Etsu Chemical Co., Ltd., dimethicone/phenyl vinyl dimethicone crosspolymer of (KSG-18 and so on) manufactured by Shin-Etsu Chemical Co., Ltd., vinyl dimethicone/lauryl dimethicone crosspolymer of (KSG-41 and so on) manufactured by Shin-Etsu Chemical Co., Ltd., and dimethicone crosspolymer assigned in INCI may be used. Furthermore, as the non-emulsifiable silicone elastomer, dimethicone/vinyl dimethicone crosspolymer of (KMP-400 and so on) manufactured by Shin-Etsu Chemical Co., Ltd., and vinyl dimethicone/methicone silsesqioxane crosspolymer of (KMP-100 and so on) manufactured by Shin-Etsu Chemical Co., Ltd. may be also used.

By containing the non-emulsifiable silicone elastomer, the cosmetic that has further increased emulsion stability, no-stickiness, excellent makeup durability and moist feeling may be obtained.

In the cosmetic of the present invention, alcohols, solids, semisolids or liquid oils (other than the silicone oils illustrated above), and water that are usually used in the cosmetics may be added. Although examples are shown below, the present invention is not limited to these.

As alcohols that may be used in the present invention, ethanol, propanol, ethylene glycol, ethylene glycol monoalkyl ether, diethylene glycol monoethyl ether, polyethylene glycol, propylene glycol, dipropylene glycol, 1,3-butylene glycol, glycerin, diglycerin, polyglycerin, pentaerythritol, sucrose, lactose, xylitol, sorbitol, mannitol, maltitol, carrageenan, agar, guar gum, dextrin, tragacanth gum, locust bean gum, polyvinyl alcohol, polyoxyethylene-based polymer, polyoxyethylene-polyoxypropylene copolymer-based polymer, hyaluronic acid, chondroitin sulfate, and chitin chitosan may be used, and as needs arise, these may be used singularly or in a combination of two or more kinds thereof. A content of the alcohols in the cosmetic is usually 0.1 to 90.0 mass %, and preferably 0.5 to 50.0 mass %. In the case of 0.1 mass % or larger, it is enough for moisture retention, antimicrobial, mildewproofing effects, and in the case of 90.0 mass % or smaller, the effect of the cosmetic of the present invention may be sufficiently exhibited.

Examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, polyoxyethylene cholesterol ether, glycerol monostearyl ether (batyl alcohol) and monooleyl glyceryl ether (selachyl alcohol).

As oils other than silicone oils that may be used in the present invention, what is shown below is illustrated. Here, POE means polyoxyethylene.

As natural animal and vegetable oils and fats and semi-synthetic oils, avocado oil, linseed oil, almond oil, Ivo Tulloh, perilla oil, olive oil, Cacao oil, kapok wax, kaya oil, carnauba wax, liver oil, candelilla wax, beef tallow, beef foot oil, beef bone fat, hardening beef tallow, apricot kernel oil, spermaceti wax, hydrogenated oil, wheat germ oil, sesame oil, rice germ oil, rice bran oil, cane wax, sasanqua oil, safflower oil, shea butter, China Gili oil, cinnamon oil, shellac wax, turtle oil, soybean oil, tea seed oil, camellia oil, oenotherae biennis oil, corn oil, lard, rapeseed oil, Japanese tung oil, bran wax, germ oil, horse fat, palm oil, palm kernel oil, castor oil, hydrogenated castor oil, castor oil fatty acid methyl ester, sunflower oil, grape oil, bayberry wax, Jojoba oil, macadamia-nuts oil, yellow-bees-wax, mink oil, cotton-seed-cake-oil, cotton wax, Japan wax, Japan-wax-kernel-oil, montan wax, palm oil, hardening palm oil, bird palm-oil-fatty-acid glyceride, mutton tallow, peanut oil, lanolin, liquefied lanolin, reduced lanolin, lanolin alcohol, hard lanolin, lanolin acetate, lanolin fatty acid isopropyl ester, POE lanolin alcohol ether, POE lanolin alcohol acetate, lanolin fatty acid polyethylene glycol ester, POE hydrogenated lanolin alcohol ether, and egg yolk oil may be used.

Examples of the hydrocarbon oils include Ozocerite, squalane, squalene, ceresin, paraffin, paraffin wax, isodecane, isododecane, isohexadecane, liquid paraffin, pristane, polyisobutylene, microcrystalline wax, and Vaseline. Examples of higher fatty acid include lauric acid, myristic acid, palmitic acid, stearic acid, behenic acid, undecylenic acid, oleic acid, linolic acid, linolenic acid, arachidonic acid, eicosapentaenoic acid, docosahexaenoic acid, isostearic acid and 12-hydroxystearic acid.

Examples of the ester oil include diisobutyl adipate, 2-hexyldecyl adipate, 2-heptylundecyl adipate, N-alkyl glycol monoisostearate, isocetyl isostearate, trimethylolpropane triisostearate, ethylene glycol di-2-ethylhexanoate, neopentyl glycol di-2-ethyl hexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprylate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, fatty acid esters of dipentaerythritol, isononyl isononanoate, triisohexanoin, isopropyl myristate, 2-octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, diisostearyl malate, dextrin palmitate, dextrin stearate, dextrin palmitate 2-ethylhexanoate, glucose palmitate, glucose stearate, monobenzylidene sorbitol, and dibenzylidene sorbitol.

As the glyceride oils, examples thereof include acetoglyceryl, glyceryl diisooctanoate, glyceryl triisostearate, glyceryl triisopalmitate, glyceryl tri-2-ethylhexanoate, glyceryl monostearate, glyceryl di-2-heptylundecanoate, and glyceryl trimyristate.

These oils other than silicone oils may be used singularly or in a mixture of two or more kinds as needs arise. In the cosmetic of the present invention, the oil may be contained in the range of 0 to 90 mass %, particularly preferably in the range of 1 to 90 mass % of an entirety of the cosmetic.

An amount of water used when water is contained as a constituent of the cosmetic of the present invention is 1 to 99 mass %.

Although the cosmetics of the present invention may be formed into excellent ones with only the above constituents, furthermore, as needs arise, the following components i), ii) and iii) may be added.

i) Powder and/or Colorant Illustrated Below

Examples of inorganic powder include titanium dioxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, black mica, silicic acid, silicic anhydride, aluminum silicate, magnesium silicate, magnesium aluminum silicate, calcium silicate, barium silicate, strontium silicate, tungstic acid metal salt, hydroxyapatite, vermiculite, hijilite, bentonite, montmorillonite, hectorite, zeolite, ceramic powder, calcium monohydrogen phosphate, alumina, aluminum hydroxide, boron nitride, and silica.

Examples of the organic powder include polyamide powder, polyester powder, polyethylene powder, polypropylene powder, polystyrene powder, polyurethane powder, benzoguanamine powder, polymethyl benzoguanamine powder, tetrafluoroethylene powder, polymethylmethacrylate powder, cellulose powder, silk powder, nylon powder such as 12 nylon and 6 nylon, and other powders of styrene/acrylic acid copolymer, divinyl benzene/styrene copolymer, vinyl resin, urea resin, phenol resin, fluororesin, silicon resin, acrylic resin, melamine resin, epoxy resin, polycarbonate resin, micro crystallite fiber powder, starch, and lauroyl lysine.

Examples of surfactant metal salt powder (metal soap) include zinc stearate, aluminum stearate, calcium stearate, magnesium stearate, zinc myristate, magnesium myristate, zinc cetyl phosphate, calcium cetyl phosphate, and zinc sodium cetyl phosphate.

Examples of the colored pigment include: inorganic red system pigments such as iron oxide, iron hydroxide, and iron titanate; inorganic brown system pigments such as gamma-iron oxide; inorganic yellow system pigments such as yellow iron oxide and ocher; inorganic black system pigments such as black iron oxide and carbon black; inorganic violet system pigments such as manganese violet and cobalt violet; inorganic green system pigments such as chromium hydroxide, chromium oxide, cobalt oxide, and cobalt titanate; inorganic blue system pigments such Prussian blue, and ultramarine; laked one of tar system pigment; laked one of natural coloring matter; and composite powder obtained by complexing these powders.

Examples of pearl pigments include titania-clad mica, bismuth oxychloride, titania-clad bismuth oxychloride, titania-clad talc, argentine, and titania-clad colored mica. Examples of the metal powder pigment include aluminum powder, copper powder and stainless powder.

Examples of tar dye include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207. Examples of the natural dye include carminic acid, laccaic acid, carthamin, brazilin, and crocin.

If these are used in normal cosmetics, irrespective of their shapes (spherical, needle-like, plate-like), particle sizes (foggy, fine particle, pigment class), and particle structures (porous, non-porous), any of these may be used. Furthermore, other than that these powders may be complexed each other, a surface treatment may be applied with oils, silicones that are not represented by the general formula (1), or fluoro-compounds and so on.

A blending amount when using above illustrated powders and/or colorants is preferably 0 to 99 mass %, particularly preferably 0.1 to 99 mass % relative to a total amount of the cosmetic.

ii) Surfactants Illustrated Below

Examples of surfactant include saturated or unsaturated fatty acid soaps such as sodium stearate and triethanolamine oleate; carboxylates such as an alkyl ether carboxylic acid and it's salt and a condensate between an amino acid and a fatty acid; an amide ether carboxylate, an alpha-sulfo fatty acid ester salt, an alpha-acyl sulfonate, an alkyl sulfonate, an alkene sulfonate, a sulfonate of fatty acid ester, a sulfonate of fatty acid amide, an alkyl sulfonate and a sulfonate of it's formalin condensate, an alkyl sulfate ester salt, a secondary higher alcohol sulfate ester salt, an alkyl and aryl ether sulfate ester salt, a sulfate ester salt of fatty acid ester, a sulfate ester salt of a fatty acid alkylol amide, sulfate ester salts of a Turkey red oil and so on, an alkyl phosphate, an alkenyl phosphate, an ether phosphate, an alkyl allyl ether phosphate, an alkyl amide phosphate, and a N-acyl amino acid-based activator.

Examples of cationic surfactant include: an alkylamine salt, an amine salt of a polyamine, an amino alcohol fatty acid derivative and so on; an alkyl quaternary ammonium salt, an aromatic quaternary ammonium salt, a pyridinium salt, and an imidazolium salt.

Examples of nonionic surfactant include a sorbitan fatty acid ester, a glycerin fatty acid ester, a polyglycerin fatty acid ester, a propylene glycol fatty acid ester, a polyethylene glycol fatty acid ester, a sucrose fatty acid ester, a polyoxyethylene alkyl ether, a polyoxypropylene alkyl ether, a polyoxyethylene alkyl phenyl ether, a polyoxyethylene fatty acid ester, a polyoxyethylene sorbitan fatty acid ester, a polyoxyethylene sorbitol fatty acid ester, a polyoxyethylene glycerin fatty acid ester, a polyoxyethylene propylene glycol fatty acid ester, a polyoxyethylene castor oil, a polyoxyethylene hard castor oil, a polyoxyethylene phytostanol ether, a polyoxyethylene phytosterol ether, a polyoxyethylene cholestanol ether, a polyoxyethylene cholesteryl ether, a polyoxyalkylene-modified organopolysiloxane, a polyoxyalkylene/alkyl-comodified organopolysiloxane, a polyoxyalkylene/fluoroalkyl-comodified organopolysiloxane block copolymer, an alkanol amide, a sugar ether, and a sugar amide. Examples of the amphoteric surfactant includes a betaine, an aminocarboxylic acid salt, and an imidazoline derivative.

A blending amount when the above-illustrated surfactant is used is preferably 0.1 to 20 mass % and particularly preferably 0.2 to 10 mass % relative to a total amount of the cosmetic.

iii) Graft or Block Copolymer of Acryl/Silicone, and Silicone Resin Such as Silicone Network Compound In the cosmetic of the present invention, depending on the object thereof, at least one kind of silicone resin selected from a graft or block copolymer of acryl/silicone and a silicone network compound may be also used. In the present invention, the silicone resin is particularly preferable to be an acryl silicone resin. Furthermore, the silicone resin is preferable to be an acrylsilicone resin containing at least one kind selected from the group consisting of a pyrrolidone moiety, a long-chain alkyl moiety, a polyoxyalkylene moiety and a fluoroalkyl moiety in a molecule. Furthermore, the silicone resin is preferably a silicone network compound. A blending amount in the case of using a silicone resin such as the graft or block copolymer of acryl/silicone or the silicone network compound like this is preferably 0.1 to 20 mass %, and particularly preferably 1 to 10 mass % relative to a total amount of the cosmetic.

Furthermore, other than the above, a UV-absorber usually used in the cosmetic may be added in the cosmetic of the present invention. The cosmetic containing the silicone compound represented by the average composition formula (1) of the present invention may secure excellent emulsion stability even under the presence of the UV-absorber. Examples of the UV-absorber include a benzoic acid UV-absorber such as para-amino benzoic acid; an anthranilic acid UV-absorber such as methyl anthranilate; a salicylic UV-absorber such as methyl salicylate; a cinnamic acid UV-absorber such as octyl para-methoxy cinnamate; a benzophenone UV-absorber such as 2,4-dihydroxybenzophenone; a urocanic acid UV-absorber such as ethyl urocanate; and a dibenzoylmethane UV-absorber such as 4-t-butyl-4'-methoxy-dibenzoylmethane.

Furthermore, other than the above, a water-soluble polymer, a skin-forming agent, an oil-soluble gelling agent, an organic modified clay ore, a resin, a moisturizer, an antiseptic agent, an anti-bacterial agent, a perfume, salts, an antioxidant, a pH-adjusting agent, a chelate agent, an algefacient, an anti-inflammatory drug, a skin beautification component, vitamins, amino acids, a nucleic acid, a hormone, and inclusion compounds, which are usually used in the cosmetics may be added to the cosmetics of the present invention.

As specific applications of the cosmetics of the present invention, a skin care product, a make-up product, a UV-proof product, an antiperspirant, and a health care product are preferably cited. Furthermore, although there is no particular limitation on the forms of the products, the cosmetic may be in the form of a liquid, an emulsion, a cream, a solid, a paste, a gel, a powder, a multilayer, a mousse, and a spray.

EXAMPLES

In what follows, the present invention will be described with reference to Examples and Comparative Examples, but, the present invention is not limited by these Examples. Furthermore, in a step 1, disappearance of Si—H and generation of Si—OH were confirmed with a Fourier transformation infrared spectrophotometer (FT-IR). A $^1$H-NMR analysis was performed by using AVANCE-III (manufactured by Brucker Biospin Co., Ltd.) with chloroform-d as a measurement solvent.

Furthermore, in the Examples and Comparative Examples, a purity of a reaction product was confirmed by gas chromatography equipped with a thermal conductivity type detector under the following condition.

Measurement Condition of Gas Chromatography (GC)
Gas chromatograph: manufactured by Agilent Technologies
Detector: FID (Flame Ionization Detector)
Temperature: 300° C.
Capillary column: J&W Corp. HP-5MS (0.25 mm×30 m×0.25 μm)
Temperature increase program: 50° C. (2 minutes)→10° C./minute→250° C. (keep)
Inlet port temperature: 250° C.
Carrier gas: helium (1.0 ml/minute)
Split ratio: 50:1
Charge amount: 1 μl (Synthesis Example 1) Synthesis of Branched Organopolysiloxane Having $C_nH_{(2n-1)}$-Group (Step 1)

In a reactor, 64 g of tetrahydrofuran, 107 g of tris(trimethylsiloxy)silane, and 0.011 g of palladium-carbon (30 wt % supported on activated carbon) were charged, and an internal temperature was set to 10° C. or lower by cooling with an ice water bath. Hereto, 9.45 g of water was added, and a solution was stirred at an internal temperature of 5 to 10° C. for 1 hour, followed by gradually increasing the temperature, further followed by stirring for 12 hours at 25° C. A reaction liquid was filtered with a filter paper, a solvent was removed by an evaporator, and a compound A of the purity of 96% was obtained. A yield was 93%. Then, the FT-IR was measured, from disappearance of a peak of 2200 to 2300 cm$^{-1}$ and generation of a peak of 3500 to 3700 cm$^{-1}$, it was confirmed that a target object was obtained.

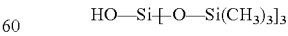 [Compound A]

(Step 2)

In a reactor, 71 g of a compound A, 313 g of n-hexane, and 24.3 g of triethyl amine were charged, and an internal temperature was set to 15° C. or lower by cooling with an ice water bath. Hereto, 28.8 g of dimethyl vinyl chlorosilane was dropped while maintaining the internal temperature at 5 to 15° C., followed by stirring at 20 to 23° C. for 12 hours.

A reaction liquid was washed twice with 400 g of water, followed by vacuum concentration, and a compound B of the purity of 98% was obtained. A yield was 88%.

1HNMR: 6.09 to 6.19 ppm (1H, m), 5.89 to 5.99 ppm (1H, d), 5.70 to 5.79 ppm (1H, d), −0.18 to 0.32 ppm (33H, m)

[Compound B]

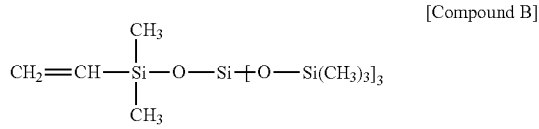

(Synthesis Example 2) Synthesis of Branched Organopolysiloxane Having $C_nH_{(2n-1)}$-Group (Step 1)

In a 3000 ml separable flask equipped with a stirrer, a reflux condenser, a dropping funnel and a thermometer, 500 g of tetrahydrofuran, 122 g of water, and 0.3 g of palladium-carbon (30 wt % supported on activated carbon) were charged, followed by cooling with an ice water bath, and an internal temperature was set to 10° C. or lower. 500 g of 1, 1, 1, 3, 5, 5, 5-heptamethyltrisiloxane was dropped while keeping the internal temperature at 5 to 10° C., followed by stirring at 25° C. for 6 hours. A reaction liquid was filtered with a filter paper and distilled after vacuum concentration, and a compound C of purity of 98.4% was obtained as a fraction of a boiling point 91 to 99° C./42 to 43 mmHg. A yield was 92%. By measuring the FT-IR, from disappearance of a peak of 2100 to 2200 cm$^{-1}$ and generation of a peak of 3500 to 3700 cm$^{-1}$, it was confirmed that a target object was obtained.

[Compound C]

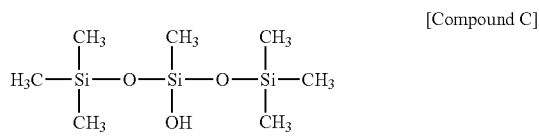

(Step 2)

In a 2000 ml separable flask equipped with a stirrer, a reflux condenser, a dropping funnel and a thermometer, 303.8 g of the compound C, 500 g of n-hexane, and 124.4 g of triethylamine were charged, followed by cooling with an ice water bath, and an internal temperature was set to 15° C. or lower. Hereto, 86 g of methylvinyldichlorosilane was dropped while keeping the internal temperature at 5 to 10° C., followed by stirring at 15 to 20° C. for 12 hours. After washing the obtained reaction liquid twice with water of 400 g, a solvent was distilled away by an evaporator, and a compound D of purity of 95% was obtained. A yield was 97%.

1HNMR: 6.09 to 6.19 ppm (1H, m), 5.89 to 5.99 ppm (1H, d), 5.70 to 5.79 ppm (1H, d), −0.18 to 0.32 ppm (45H, m)

[Compound D]

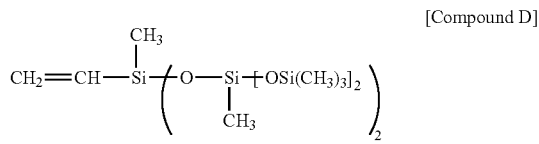

Next, Examples and Comparative Examples in which the compound B and compound D were used will be described. In the following composition formula, a Me$_3$SiO group (or Me$_3$Si group) is represented by "M", a Me$_2$SiO group is represented by "D", a HMeSiO group is represented by "H", and units obtained by modifying a methyl group in the M and D with any substituent R are represented by M$^R$ and D$^R$.

Example 1

In a reactor, 100 g of organohydrogensiloxane represented by an average composition formula M$_2$D$_{42}$H$_3$ and 23 g of the compound B were charged, 0.05 g of an isopropyl alcohol solution of 0.5 mass % of chloroplatinic acid was added, followed by reacting at the internal temperature of 80° C. for 1 hour.

Next, 6.7 g of triglycerinmonoallylether, 0.08 g of isopropyl alcohol solution of 0.5 mass % of chloroplatinic acid and 58.4 g of isopropyl alcohol were charged, followed by reacting for 5 hours under reflux of the solvent. An obtained reactant was heated under reduced pressure to distill away the solvent, and a silicone compound (I) represented by an average composition formula M$_2$D$_{42}$D$^{R21}_2$D$^{R31}$ having a weight average molecular weight of 7500 was obtained at a yield of 90%. In the formula, R21 and R31 represent the following.

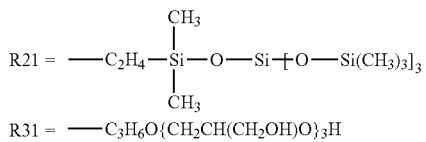

Example 2

Into a reactor, 100 g of organohydrogensiloxane represented by an average composition formula M$_2$D$_{70}$H$_7$ and 27.5 g of the compound B were charged, 0.05 g of an isopropyl alcohol solution of 0.5 mass % of chloroplatinic acid was added, followed by reacting at the internal temperature of 80° C. for 1 hour.

Next, 9.1 g of diglycerinmonoallylether, 0.08 g of isopropyl alcohol solution of 0.5 mass % of chloroplatinic acid and 61.4 g of isopropyl alcohol were charged, followed by reacting for 5 hours under reflux of the solvent. Next, 19.8 g of aq. hydrochloric acid of 0.005N was added to hydrolyze allyl ether groups of unreacted diglycerinmonoallylether, followed by neutralizing with 0.2 g of aq. sodium bicarbonate of 5 mass %. Then, by distilling away the solvent by heating under reduced pressure, a silicone compound (II) represented by an average composition formula M$_2$D$_{70}$D$^{R21}_4$D$^{R32}_3$ having a weight average molecular weight of 9200 was obtained at a yield of 92%. In the formula, R21 is the same as described above and R32 represents the following.

R32=-C$_3$H$_6$O{CH$_2$CH(CH$_2$OH)O}$_2$H

Example 3

Into a reactor, 100 g of organohydrogensiloxane represented by an average composition formula M$_2$D$_{35}$H$_{21}$ and 12.2 g of triglycerinmonoallylether, 106.3 g of isopropyl alcohol, and 0.06 g of an isopropyl alcohol solution of 0.5 mass % of chloroplatinic acid were added, followed by reacting for 3 hours under reflux of the solvent.

Next, after adding 57.4 g of a compound D and reacting for 1 hour, 66.5 g of 1-dodesen and 0.14 g of isopropyl alcohol solution of 0.5 mass % of chloroplatinic acid were added, followed by reacting for further 5 hours. By heating under reduced pressure to distill away the solvent, a silicone compound (III) represented by an average composition formula $M_2D_{35}D^{R22}{}_4D^{R31}{}_2D^{C12}{}_{1.5}$ having a weight average molecular weight of 10800 was obtained at a yield of 89%. In the formula, R31 is the same as described above and R22 represents the following.

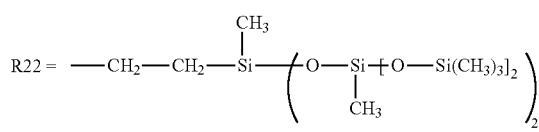

Example 4

Into a reactor, 100 g of organohydrogensiloxane represented by $H_4$, 96.7 g of glycerin monoallyl ether, 453 g of a compound D and 300 g of isopropyl alcohol were mixed, to this mixture, 0.4 g of an isopropyl alcohol solution of 0.5 mass % of chloroplatinic acid was added, followed by reacting for 6 hours under reflux of the solvent. A reactant was heated under reduced pressure to distill away the solvent, followed by filtering, and a silicone compound (IV) represented by $D^{R22}{}_2D^{R33}{}_2$ and having a weight average molecular weight of 1800 was obtained at a yield of 93%. The R22 is the same as described above and R33 represents the following.

R33=-C$_3$H$_6$OCH$_2$CH(CH$_2$OH)OH

Example 5

In a reactor, 100 g of organohydrogensiloxane represented by an average composition formula $M_2D_{42}H_3$, 11.5 g of the compound B and 17.9 g of $MM^{R23}D_6$ were charged, 0.05 g of an isopropyl alcohol solution of 0.5 mass % of chloroplatinic acid was added, followed by reacting at the internal temperature of 80° C. for 1 hour.

Next, 6.7 g of triglycerinmonoallylether, 0.08 g of isopropyl alcohol solution of 0.5 mass % of chloroplatinic acid and 63.2 g of isopropyl alcohol were charged, followed by reacting for 5 hours under reflux of the solvent. An obtained reactant was heated under reduced pressure to distill away the solvent, and a silicone compound (V) represented by an average composition formula $M_2D_{42}D^{R21}D^{R24}D^{R31}$ having a weight average molecular weight of 8100 was obtained at a yield of 90%. In the formula, R21 and R31 are the same as those described above, and R23 and R24 represent the following.

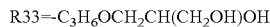

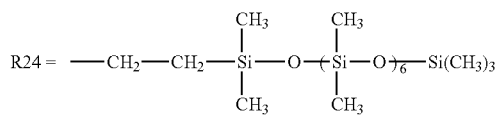

Example 6

In a reactor, 100 g of organohydrogensiloxane represented by an average composition formula $M_2D_{400}H_5$, 2.3 g of triglycerinmonoallylether, 160 g of isopropyl alcohol and 0.06 g of an isopropyl alcohol solution of 0.5 mass % of chloroplatinic acid were added, followed by reacting for 3 hours under reflux of the solvent.

Next, 2.63 g of the compound B and 0.04 g of isopropyl alcohol solution of 0.5 mass % of chloroplatinic acid were charged, followed by reacting for further 5 hours. By distilling away the solvent by heating under reduced pressure, a silicone compound (VI) represented by an average composition formula $M_2D_{400}D^{R21}{}_2D^{R31}{}_3$ having a weight average molecular weight of 51000 was obtained at a yield of 92%. In the formula, R21 and R31 are the same as those described above.

Comparative Example 1

In a reactor, 100 g of organohydrogensiloxane represented by an average composition formula $M_2D_{42}H_3$, and 35.8 g of $MM^{R23}D_6$ were charged, 0.05 g of an isopropyl alcohol solution of 0.5 mass % of chloroplatinic acid was added, followed by reacting for 1 hour at the internal temperature of 80° C.

Next, 6.7 g of triglycerinmonoallylether, 0.08 g of isopropyl alcohol solution of 0.5 mass % of chloroplatinic acid and 64.5 g of isopropyl alcohol were charged, followed by reacting for 5 hours under reflux of the solvent. An obtained reactant was heated under reduced pressure to distill away the solvent, and a silicone compound (VII) represented by an average composition formula $M_2D_{42}D^{R24}{}_2D^{R31}$ having a weight average molecular weight of 9030 was obtained at a yield of 93%. In the formula, R24 and R31 are the same as those described above.

Comparative Example 2

In a reactor, 100 g of organohydrogensiloxane represented by an average composition formula $M_2D_{70}H_7$, and 42.9 g of $MM^{R23}D_6$ were charged, 0.05 g of an isopropyl alcohol solution of 0.5 mass % of chloroplatinic acid was added, followed by reacting for 1 hour at the internal temperature of 80° C.

Next, 9.1 g of diglycerinmonoallylether, 0.09 g of an isopropyl alcohol solution of 0.5 mass % of chloroplatinic acid and 68.4 g of isopropyl alcohol were charged, followed by reacting for 5 hours under reflux of the solvent. Then, 22.0 g of aq. hydrochloric acid of 0.005N was added to hydrolyze allyl ether groups of unreacted diglycerinmonoallylether, followed by neutralizing with 0.2 g of aq. sodium bicarbonate of 5 mass %. Next, by distilling away the solvent by heating under reduced pressure, a silicone compound (VIII) represented by an average composition formula $M_2D_{70}D^{R24}{}_4D^{R32}{}_3$ having a weight average molecular weight of 10200 was obtained at a yield of 90%. In the formula, R24 and R32 are the same as those described above.

Examples 7 and 8, Comparative Examples 3 and 4

According to combinations shown in the following Table 1, water in oil emulsions were prepared, followed by evaluating according to an evaluation method and evaluation criteria shown below. Results thereof are also shown in Table 1. Additionally, OMC is 4-methoxycinnamic acid 2-ethylhexyl ester.

TABLE 1

| Component | | Example 7 | Example 8 | Comparative Example 3 | Comparative Example 4 |
|---|---|---|---|---|---|
| 1 | Silicone compound (II) | 2 | 2 | | |
| | Silicone compound (VIII) | | | 2 | 2 |
| 2 | Dimethylpolysiloxane (6 mm$^2$/s) | 25 | 15 | 25 | 15 |
| 3 | OMC | | 10 | | 10 |
| 4 | Sodium chloride | 0.5 | 0.5 | 0.5 | 0.5 |
| 5 | 1.3-butylene glycol | 5 | 5 | 5 | 5 |
| 6 | Purified water | 69.5 | 69.5 | 69.5 | 69.5 |
| Stability (immediately after preparation) | | ○ | ○ | ○ | ○ |
| Stability (50° C./one day) | | ○ | ○ | ○ | ○ |
| Stability(50° C./3 days) | | ○ | ○ | ○ | Δ |
| Stability (50° C./10 days) | | ○ | ○ | ○ | x |
| (1) Spreadability during application | | A | A | A | D |
| (2) Smoothness of a skin after application | | A | A | A | D |

(Preparation Method of Water-in-Oil Emulsion)
A. Components 1 to 3 are homogeneously mixed.
B. Components 4 to 6 are homogeneously mixed.
C. Emulsifying while adding the B to the A with stirring.
(Evaluation Criteria)
1. Temporal Stability
(Evaluation Method)
Immediately after preparation, and, after storing for one day, three days and ten days at 50° C., states were visually observed and evaluated according to the following criteria.
○ (circle): Separation was not found and a uniform emulsion.
Δ (delta): Slight separation of oil was found in an upper layer.
X (cross): The separation was found.
2. Sensory Evaluation
(1) Spreadability During Application, (2) Smoothness of a Skin after Application
  (Method of Evaluation)
Each of samples was used by a professional panel of 8 members, and (1) spreadability during application and (2) smoothness of a skin after application were asked to evaluate according to the following evaluation criteria.
5 point: excellent
4 point: good
3 point: ambiguous
2 point: slightly poor
1 point: bad
Average points obtained by the above evaluation were judged according to the criteria shown below. Results are shown in Table 1.
Judgement of the obtained average points:
Obtained average point is 4.5 point or higher
  A
Obtained average point is 3.5 point or higher and lower than 4.5 point
  B
Obtained average point is 2.5 point or higher and lower than 3.5 point
  C
Obtained average point is 1.5 point or higher and lower than 2.5 point
  D
Obtained average point is lower than 1.5 point
  E
As shown in Table 1, it was confirmed that the silicone compound (II) used in Examples 7, 8 exhibits higher temporal stability even during OMC addition, and has excellent spreadability during application and smoothness of a skin after application than the silicone compound (VIII) used in Comparative Examples 3, 4.

Examples 9 to 12, Comparative Examples 5 and 6

According to combinations shown in the following Table 2, powder dispersions were prepared, followed by evaluating according to an evaluation method and evaluation criteria shown below. Results thereof are also shown in Table 2. The evaluation method is the same as that described above.
(Combinations)

(Examples 9, 10, Comparative Example 5)
  MTR-07/Dispersant (Silicone Compound)/Cyclopentasiloxane (Note 1)=40/10/50

(Examples 11, 12, Comparative Example 6)
  Mz506X/Dispersant (Silicone Compound)/Cyclopentasiloxane (Note 1)/OMC=55/5/30/10
(Note 1) Manufactured by Shin-Etsu Chemical Co., Ltd.: KF-995
(Preparation Method)
Paint shaker/15 h (beads 150 g)

TABLE 2

| | Example 9 | Example 10 | Example 11 | Example 12 | Comparative Example 5 | Comparative Example 6 |
|---|---|---|---|---|---|---|
| Aluminum hydroxide/stearic acid-treated titanium dioxide (MTR-97) | 40 | 40 | | | 40 | |

TABLE 2-continued

|  | Example 9 | Example 10 | Example 11 | Example 12 | Comparative Example 5 | Comparative Example 6 |
|---|---|---|---|---|---|---|
| Triethoxysilylethylpolydimethylsiloxyethyl-hexyldimethicone (Note 2)-treated zinc oxide (Mz 506X) |  |  | 55 | 55 |  | 55 |
| Silicone compound (I) | 10 |  | 5 |  |  |  |
| Silicone compound (V) |  | 10 |  | 5 |  |  |
| Silicone compound (VII) |  |  |  |  | 10 | 5 |
| OMC |  |  | 10 | 10 |  | 10 |
| KF-995 | 50 | 50 | 30 | 30 | 50 | 30 |
| Stability (immediately after preparation) | ○ | ○ | ○ | ○ | ○ | ○ |
| Stability (50° C./one day) | ○ | ○ | ○ | ○ | ○ | Δ |
| Stability (50° C./3 days) | ○ | ○ | ○ | ○ | ○ | x |
| Stability (50° C./10 days) | ○ | ○ | ○ | Δ | ○ | x |
| (1) Spreadability during application | A | B | A | B | A | D |
| (2) Smoothness of a skin after application | A | A | B | A | A | D |

(Note 2)
Manufactured by Shin-Etsu Chemical Cp., Ltd.: KF-9909

As shown in Table 2, it was confirmed that the silicone compound (I) and silicone compound (V) used in Examples 9 to 12 provide higher temporal stability during OMC addition, and excellent usability during application and after application than the silicone compound (VII) used in Comparative Examples 5, 6.

In what follows, a formulation example of a cosmetic will be shown.

(Formulation 1) Makeup Remover

A makeup remover formed of the following components was prepared.

| (Component) | Mass (%) |
|---|---|
| 1. POE (10) sorbitan monolaurate | 10.0 |
| 2. Siloxane compound (IV) | 20.0 |
| 3. Sorbitol | 10.0 |
| 4. Carrageenan | 0.5 |
| 5. Glycerin | 5.0 |
| 6. Anti-septic | proper amount |
| 7. Perfume | proper amount |
| 8. Purified water | Balance |

(Production Method)
A: Components 1 to 6 and 8 are added and dissolved homogeneously.
B: A component 7 is added to the A to obtain a makeup remover.

When a foundation was removed with the makeup remover obtained as was described above, the makeup remover was found to have excellent familiarity with the foundation, very excellent stain removability, light spread in use, refresh feeling of a skin after use and very excellent usability and use feeling.

(Formulation Example 2): Face Wash

A face wash formed of the following components was prepared.

| (Component) | Mass (%) |
|---|---|
| 1. Polyoxyethylene (6) lauryl ether | 5.0 |
| 2. Siloxane compound (IV) | 10.0 |
| 3. Ethanol | 10.0 |
| 4. Lauryl dimethyl amine oxide | 2.0 |
| 5. Propylene glycol | 3.0 |
| 6. Anti-septic | proper amount |
| 7. Perfume | proper amount |
| 8. Purified water | Balance |
| Sum total | 100.0 |

(Production Method)
A: Components 1 to 6 and 8 are added and dissolved homogeneously.
B: A component 7 is added to the A to obtain a face wash.

When a face wash obtained as was described above was used, the face wash was found to have excellent familiarity with the cosmetic and skin grease stain, very excellent stain removability, light spread in use, refresh feeling of a skin without stickiness after use and very excellent usability and use feeling.

(Formulation Example 3) Emulsion Cream Foundation

| (Component) | Mass (%) |
|---|---|
| 1. Alkyl-modified crosslinking glycerin-modified silicone (note 1) | 2.0 |
| 2. Alkyl-modified crosslinking dimethylpolysiloxane (note 2) | 2.0 |
| 3. Liquid paraffin | 2.0 |
| 4. Trioctanoin | 5.0 |
| 5. Isotridecyl isononanoate | 9.0 |
| 6. Silicone compound (III) | 1.5 |
| 7. Hybrid silicone composite powder (note 3) | 3.0 |

-continued

| (Component) | Mass (%) |
|---|---|
| 8. Triethoxysilylethyl polydimethylsiloxyethyl hexyl dimethicone (Note 4) treated iron oxide | 2.5 |
| 9. Triethoxysilylethyl polydimethylsiloxyethyl hexyl dimethicone (Note 4) treated titanium dioxide | 7.5 |
| 10. 1,3-butylene glycol | 5.0 |
| 11. Sodium citrate | 3.0 |
| 12. Magnesium sulfate | 3.0 |
| 13. Anti-septic | proper amount |
| 14. Perfume | proper amount |
| 15. Purified water | balance |
| Sum total | 100.0 |

(note 1) Manufactured by Shin-Etsu Chemical Co., Ltd.: KSG-810
(note 2) Manufactured by Shin-Etsu Chemical Co., Ltd.: KSG-41
(note 3) Manufactured by Shin-Etsu Chemical Co., Ltd.: KSP-100
(Note 4) Manufactured by Shin-Etsu Chemical Co., Ltd.: KF-9909

(Production Method)

A: Components 1 to 6 were homogeneously mixed, and components 7 to 9 were added and homogenized.

B: Components 10 to 13 and 15 were dissolved.

C: Under stirring, the B was gradually added to the A to emulsify, followed by cooling and adding a component 14, and an emulsion cream foundation was obtained.

The emulsion cream foundation obtained like this was confirmed to have low viscosity and fine-grained finish, light spread without stickiness and greasiness, soft use feeling and shape correction effect of skin, excellent cosmetic durability, and excellent stability without temperature change and temporal change.

(Formulation Example 4): Eye Liner

| (Component) | Mass (%) |
|---|---|
| 1. Decamethylcyclopentasiloxane | 39.0 |
| 2. Siloxane compound (III) | 3.0 |
| 3. Organic silicone resin (note 1) | 15.0 |
| 4. Dioctadecyldimethylammonium salt-modified montmorillonite | 3.0 |
| 5. Methylhydrogenpolysiloxane-treated black iron oxide | 10.0 |
| 6. 1,3-butylene glycol | 5.0 |
| 7. Sodium dehydroacetate | proper amount |
| 8. Anti-septic | proper amount |
| 9. Purified water | Balance |
| Sum total | 100.0 |

(note 1) Manufactured by Shin-Etsu Chemical Co., Ltd.: KF-7312J (Production Method)

A: Components 1 to 4 were mixed, and a component 5 was added, followed by homogeneously mixing and dispersing.

B: Components 6 to 9 were mixed.

C: The B was gradually added to the A to emulsify, and an eye liner was obtained.

The eye liner obtained like this had light spread and easy drawability, refreshing feeling with pleasant cooling feeling, further usability without stickiness. Furthermore, it was confirmed that the eye liner has very excellent usability and stability without temperature change and temporal change, excellent water resistance and excellent perspiration resistance, and very excellent cosmetic durability.

(Formulation Example 5): Foundation

| (Component) | Mass (%) |
|---|---|
| 1. Decamethylcyclopentasiloxane | 45.0 |
| 2. Dimethylpolysiloxane (6 mm$^2$/s (25° C.)) | 5.0 |
| 3. Silicone compound (I) | 3.5 |
| 4. Octadecyl dimethyl benzyl ammonium salt-modified montmorillonite | 1.5 |
| 5. Hybrid silicone composite powder (note 1) | 2.0 |
| 6. Triethoxysilylethylpolydimethylsiloxyethylhexyldimethicone (note2)-treated iron oxide | 2.5 |
| 7. Triethoxysilylethylpolydimethylsiloxyethylhexyldimethicone (note2)-treated titanium dioxide | 7.5 |
| 8. Dipropylene glycol | 5.0 |
| 9. Methyl para-oxy benzoate | 0.3 |
| 10. Perfume | proper amount |
| 11. Purified water | Balance |
| Sum total | 100.0 |

(note 1) Manufactured by Shin-Etsu Chemical Co., Ltd.: KSP-105
(note 2) Manufactured by Shin-Etsu Chemical Co., Ltd.: KF-9909

(Production Method)

A: Components 1 to 4 were heated and mixed, and components 5 to 7 were added and homogenized.

B: Components 8, 9 and 11 were dissolved.

C: Under stirring, the B was gradually added to the A to emulsify, after cooling, followed by adding a component 10, and a foundation was obtained.

The foundation obtained like this was confirmed to have fine-grained finish, light spread without stickiness and greasiness, soft use feeling and shape correction effect of skin, excellent cosmetic durability, and excellent stability without temperature change and temporal change.

(Formulation Example 6): Cream Eye Shadow

| (Component) | Mass (%) |
|---|---|
| 1. Decamethylcyclopentasiloxane | 15.0 |
| 2. Dimethylpolysiloxane (6 mm$^2$/s (25° C.)) | 4.0 |
| 3. Acryl silicone resin (note 1) | 5.0 |
| 4. Siloxane compound (III) | 1.5 |
| 5. Acrylsilicone resin-treated pigment (note 2) | 16.0 |
| 6. Sodium chloride | 2.0 |
| 7. Propylene glycol | 8.0 |
| 8. Anti-septic | proper amount |
| 9. Purified water | Balance |
| Sum total | 100.0 |

(note 1) Manufactured by Shin-Etsu Chemical Co., Ltd.: KP-545L
(note 2) Manufactured by Shin-Etsu Chemical Co., Ltd.: KP-574 treatment (Preparation of Cosmetic)

A: Components 1 to 4 were mixed, and a component 5 was added, followed by homogeneously mixing and dispersing.

B: Components 6 to 9 were mixed.

C: The B was added to the A to emulsify, and an eye shadow was obtained.

The cream eye shadow obtained as shown above had light spread without greasiness and ashiness, and excellent durability.

(Formulation Example 7): Sun-Cut Cream

| (Component) | Mass (%) |
|---|---|
| 1. Crosslinked glycerin-modified silicone (note 1) | 3.0 |
| 2. Crosslinked dimethylpolysiloxane (note 2) | 2.0 |
| 3. Siloxane compound (II) | 1.0 |
| 4. Acryl silicone resin (note 3) | 7.0 |
| 5. Decamethylcyclopentasiloxane | 15.5 |
| 6. Octyl methoxycinnamate | 6.0 |
| 7. Acryl silicone resin dissolved product (note 4) | 10.0 |
| 8. Lipophilization-treated fine particle zinc oxide (note 5) | 20.0 |
| 9. 1,3-butylene glycol | 2.0 |
| 10. Sodium citrate | 0.2 |
| 11. Sodium chloride | 0.5 |
| 12. Perfume | proper amount |
| 13. Purified water | Balance |
| Sum total | 100.0 |

(note 1) Manufactured by Shin-Etsu Chemical Co., Ltd.: KSG-840
(note 2) Manufactured by Shin-Etsu Chemical Co., Ltd.: KSG-15
(note 3) Manufactured by Shin-Etsu Chemical Co., Ltd.: KF-545
(note 4) Manufactured by Shin-Etsu Chemical Co., Ltd.: KP-575
(note 5) Manufactured by Shin-Etsu Chemical Co., Ltd.: AES-3083 treatment (Preparation of Cosmetic)
A: A component 7 was added to a part of a component 5 to homogenize, a component 8 was added, followed by dispersing with a bead mill.
B: Components 1 to 4 and balance of a component 5, and a component 6 were homogeneously mixed.
C: Components 9 to 11, and a component 13 were mixed to homogenize.
D. The C was added to the B to emulsify, the A and a component 12 were added, and a sun-cut cream was obtained.

The sun-cut cream obtained like this had light spread without stickiness, refreshing usability without greasiness, and excellent durability.

(Formulation Example 8): Sun-Cut Cream

| (Component) | Mass (%) |
|---|---|
| 1. Crosslinked glycerin-modified silicone (note 1) | 2.0 |
| 2. Crosslinked dimethylpolysiloxane (note 2) | 3.0 |
| 3. Siloxane compound (V) | 1.5 |
| 4. Acryl silicone resin (note 3) | 4.5 |
| 5. Decamethylcyclopentasiloxane | 5.8 |
| 6. Dimethyldistearylammonium hectrite | 1.2 |
| 7. Titanium dioxide dispersio(note 4) | 20.0 |
| 8. Zinc oxide dispersion (note 5) | 15.0 |
| 9. 1,3-butylene glycol | 5.0 |
| 10. Sodium citrate | 0.2 |
| 11. Sodium chloride | 0.5 |
| 12. Purified water | Balance |
| Sum total | 100.0 |

(note 1) Manufactured by Shin-Etsu Chemical Co., Ltd.: KSG-810
(note 2) Manufactured by Shin-Etsu Chemical Co., Ltd.: KSG-15
(note 3) Manufactured by Shin-Etsu Chemical Co., Ltd.: KP-549
(note 4) Manufactured by Shin-Etsu Chemical Co., Ltd.: SPD-T6
(note 5) Manufactured by Shin-Etsu Chemical Co., Ltd.: SPD-Z6

(Preparation of Cosmetic)
A: Components 1 to 8 were homogeneously mixed.
B: Components 9 to 12 were mixed.
C: The B was added to the A to emulsify, and a sun-cut cream was obtained.

The sun-cut cream obtained like this had no stickiness, light spread, no greasiness, and excellent cosmetic durability.

(Formulation Example 9) Sun Tan Cream

| (Component) | Mass (%) |
|---|---|
| 1. Alkyl-modified crosslinked glycerin-modified silicone (note 1) | 4.0 |
| 2. Alkyl-modified crosslinked dimethylpolysiloxane (note 2) | 2.0 |
| 3. Silicone compound (III) | 1.0 |
| 4. Organic silicone resin (note 3) | 5.0 |
| 5. Decamethylcyclopentasiloxane | 10.5 |
| 6. Stearyl-modified acrylic silicone (note 4) | 1.0 |
| 7. Dimethyl octyl paraaminobenzoate | 1.5 |
| 8. 4-t-butyl-4'-methoxy-dibenzoyl methane | 1.5 |
| 9. Kaolin | 0.5 |
| 10. Pigment | 8.0 |
| 11. Titanium dioxide-coated mica | 8.0 |
| 12. Dioctadecyldimethylammonium chloride | 0.1 |
| 13. Sodium L-gultamate | 3.0 |
| 14. 1,3-butylene glycol | 5.0 |
| 15. Sodium citrate | 0.2 |
| 16. Sodium chloride | 0.5 |
| 17. Antioxidant | proper amount |
| 18. Anti-septic | proper amount |
| 19. Perfume | proper amount |
| 20. Purified water | balance |
| Sum total | 100.0 |

(note 1) Manufactured by Shin-Etsu Chemical Co., Ltd.: KSG-820
(note 2) Manufactured by Shin-Etsu Chemical Co., Ltd.: KSG-42
(note 3) Manufactured by Shin-Etsu Chemical Co., Ltd.: KF-7312J
(note 4) Manufactured by Shin-Etsu Chemical Co., Ltd.: KP-561P (Preparation of Cosmetic)
A: Components 1 to 8 and 17, 18 were heated and mixed.
B: A Component 12 and a part of a component 20 were heated and stirred, followed by adding components 9 to 11 hereto and dispersing.
C: Components 13 to 16 and the balances of 20 were homogeneously dissolved, followed by mixing with the B.
D: Under stirring, the C was gradually added to the A to emulsify, after cooling, followed by adding a component 19, and a sun tan cream was obtained.

The sun tan cream obtained like this had fine-grained finish, light spread without stickiness and greasiness, refreshing use feeling and excellent durability.

(Formulation Example 10): Hair Cream

| (Component) | Mass (%) |
|---|---|
| 1. Decamethylcyclopentasiloxane | 16.0 |
| 2. Methyl phenyl polysiloxane (note 1) | 2.0 |
| 3. Organic silicone resin (note 2) | 4.0 |
| 4. Squalane | 5.0 |
| 5. Acrylic silicone resin (note 3) | 2.0 |
| 6. Sorbitan sesquiisostearate | 1.5 |
| 7. Silicone compound (VI) | 2.0 |
| 8. Sodium sorbitol sulfate | 2.0 |
| 9. Sodium chondoroitin sulfate | 1.0 |
| 10. Sodium hyaluronate | 0.5 |
| 11. Propylene glycol | 3.0 |
| 12. Anti-septic | 1.5 |
| 13. Vitamin E acetate | 0.1 |
| 14. Antioxidant | proper amount |

| (Component) | Mass (%) |
|---|---|
| 15. Perfume | proper amount |
| 16. Purified water | Balance |
| Sum total | 100.0 |

(note 1) Manufactured by Shin-Etsu Chemical Co., Ltd.: KF-54
(note 2) Manufactured by Shin-Etsu Chemical Co., Ltd.: KF-7312T
(note 3) Manufactured by Shin-Etsu Chemical Co., Ltd.: KP-545

(Preparation of Cosmetic)
A: Components 1 to 7 and components 12 to 14 were homogeneously mixed.
B: Components 8 to 11 and 16 were homogeneously mixed.
C: Under stirring, the B was gradually added to the A to emulsify, followed by adding a component 15, and a hair cream was obtained.

The hair cream obtained like this had no greasiness, light spread, and excellent water resistance, water repellency, perspiration resistance and durability.

(Formulation Example 11): O/W Type Cream

| (Component) | Mass (%) |
|---|---|
| 1. Crosslinked dimethylpolysiloxane (note 1) | 8.0 |
| 2. Crosslinked methylphenylpolysiloxane (note 2) | 2.0 |
| 3. Isotridecyl isononanoate | 5.0 |
| 4. Dipropylene glycol | 7.0 |
| 5. Glycerin | 5.0 |
| 6. Methyl cellulose (2% aqueous solution) (note 3) | 7.0 |
| 7. Polyacryl amide emulsifier (note 4) | 2.0 |
| 8. Silicone compound (IV) | 0.5 |
| 9. Guanine | 1.0 |
| 10. Anti-septic | 0.1 |
| 11. Perfume | 0.1 |
| 12. Purified water | Balance |
| Sum total | 100.0 |

(note 1) Manufactured by Shin-Etsu Chemical Co., Ltd.: KSG-16
(note 2) Manufactured by Shin-Etsu Chemical Co., Ltd.: KSG-18A
(note 3) Manufactured by Shin-Etsu Chemical Co., Ltd.: Metholose SM-4000
(note 4) Manufactured by Seppic, Inc.: SEPIGEL 305

(Preparation of Cosmetic)
A: Components 1 to 3 were homogeneously mixed.
B: Components 4 to 10 and 12 were homogeneously mixed.
C: Under stirring, the A was gradually added to the B to emulsify, followed by adding a component 11, and a cream was obtained.

The cream obtained like this was found to be an O/W cream that has fine-grained finish, light spread without stickiness and greasiness, moist and fresh feeling, refreshing use feeling, very excellent cosmetic durability, and excellent stability without temperature change and temporal change.

(Formulation Example 12): O/W Emollient Cream

| (Component) | Mass (%) |
|---|---|
| 1. Crosslinked dimethylpolysiloxane (note 1) | 7.0 |
| 2. Crosslinked dimethylpolysiloxane (note 2) | 30.0 |
| 3. Acrylic silicone resin (note 3) | 3.0 |
| 4. Decamethylcyclopentasiloxane | 8.0 |
| 5. 1,3-butylene glycol | 4.0 |
| 6. Branched polyglycerin-modified silicone (note 4) | 0.6 |
| 7. Silicone compound (IV) | 0.3 |
| 8. (Acrylamide/sodium acryloyldimethyltaurate) copolymer (note 5) | 0.6 |
| 9. Dimethyl taurine ammonium acrylate/VP copolymer (note 6) | 0.7 |
| 11. Sodium chloride | 0.1 |
| 12. Purified water | 45.7 |
| Sum total | 100.0 |

(note 1) Manufactured by Shin-Etsu Chemical Co., Ltd.: KSG-15
(note 2) Manufactured by Shin-Etsu Chemical Co., Ltd.: KSG-16
(note 3) Manufactured by Shin-Etsu Chemical Co., Ltd.: KP-545
(note 4) Manufactured by Shin-Etsu Chemical Co., Ltd.: KF-6104
(note 5) Manufactured by Seppic, Inc.: SIMULGEL 600
(note 6) Manufactured by Clariant, Ltd.: ARISTOFLEX AVC (Preparation of Cosmetic)
A: Components 1 to 4 were homogeneously mixed.
B: Components 5 to 11 were homogeneously mixed.
C: Under stirring, the A was gradually added to the B to emulsify, and an O/W emollient cream was obtained.

The O/W emollient cream obtained like this had refreshing feeling without greasiness, light spread, and a lasting skin protecting effect.

(Formulation Example 13) Lip Stick

| (Component) | Mass (%) |
|---|---|
| 1. Candelilla wax | 8.0 |
| 2. Polyethylene wax | 8.0 |
| 3. Long chain alkyl-containing acrylic silicone resin (note 1) | 12.0 |
| 4. Methyl phenyl polysiloxane (note 2) | 3.0 |
| 5. Tridecyl isononanoate | 20.0 |
| 6. Glyceryl isostearate | 16.0 |
| 7. Silicone compound (III) | 0.5 |
| 8. Octadecyldimethylbenzylammonium salt-modified montmorillonite | 0.5 |
| 9. Polyglycery triisostearate | 27.3 |
| 10. Red 202 treated with silicone (note 3) | 0.8 |
| 11. Colcothar treated with silicone (note 3) | 1.5 |
| 12. Yellow iron oxide treated with silicone (note 3) | 1.0 |
| 13. Black iron oxide treated with silicone (note 3) | 0.2 |
| 14. Titanium dioxide treated with silicone (note 3) | 1.0 |
| 15. Anti-septic | 0.1 |
| 16. Perfume | 0.1 |
| Sum total | 100.0 |

(note 1) Manufactured by Shin-Etsu Chemical Co., Ltd.: KP-561P
(note 2) Manufactured by Shin-Etsu Chemical Co., Ltd.: KF-54
(note 3) Manufactured by Shin-Etsu Chemical Co., Ltd.: KP-541

(Preparation of Cosmetic)
A: Components 1 to 8 and a part of 9 were dissolved by heating and mixing.
B: Components 10 to 16 and a balance of 9 were homogeneously mixed, followed by being added to the A and homogenized.

The lip stick obtained like this had surface luster, light spread without greasiness and ashiness, and refreshing usability. Furthermore, the water resistance and water repellent property were excellent, durability was excellent, and the stability was also excellent.

(Formulation Example 14) Powder Foundation

| (Component) | Mass (%) |
|---|---|
| 1. Vaseline | 2.5 |
| 2. Squalane | 3.0 |
| 3. Silicone compound (VI) | 0.5 |
| 4. Glyceryl trioctanoate | 2.0 |
| 5. Mica treated with silicone (note 1) | 40.0 |
| 6. Talc treated with silicone (note 1) | 22.2 |
| 7. Titanium dioxide treated with silicone (note 1) | 10.0 |
| 8. Fine particle titanium dioxide treated with silicone (note 1) | 5.0 |
| 9. Barium sulfate treated with silicone (note 1) | 10.0 |
| 10. Pigment | 0.1 |
| 11. Phenyl-modified hybrid silicone composite powder (note 2) | 2.0 |
| 12. Silicone powder (note 3) | 2.5 |
| 13. Anti-septic | 0.1 |
| 14. Perfume | 0.1 |
| Sum total | 100.0 |

(note 1) Manufactured by Shin-Etsu Chemical Co., Ltd.: KP-541
(note 2) Manufactured by Shin-Etsu Chemical Co., Ltd.: KSP-300
(note 3) Manufactured by Shin-Etsu Chemical Co., Ltd.: KMP-590

(Preparation of Cosmetic)
A: Components 5 to 12 were homogeneously mixed.
B: Components 1 to 4 and 13 were homogeneously mixed, followed by adding to the A.
C: After adding the component 14, followed by press molding in a metal mold, and a powder foundation was obtained.

The powder foundation obtained like this was found to be a powder foundation that has no stickiness, light spread, excellent adhesiveness, excellent cosmetic durability, and finish with luster.

It must be noted here that the present invention is not limited to the embodiments as described above. The foregoing embodiments are mere examples; any form having substantially the same composition as the technical idea described in claims of the present invention and showing similar effects is included in the technical scope of the present invention.

The invention claimed is:

1. A silicone compound represented by the following average composition formula (1) and having a weight average molecular weight of 500 to 200000, $$R^1{}_a R^2{}_b R^3{}_c R^4{}_d SiO_{(4-a-b-c-d)/2} \tag{1}$$

wherein, "a", "b", "c", and "d" each is $1.0 \leq a \leq 2.5$, $0.001 \leq b \leq 1.5$, $0.001 \leq c \leq 1.5$, and $0 \leq d \leq 1.0$, $R^1$ represents an organic group of the same kind or different kinds each other selected from an organic group represented by an alkyl group, an aryl group, an aralkyl group, and a fluorine-substituted alkyl group having 1 to 30 carbon atoms, and a general formula $$-C_l H_{2l} - O - R^5, \tag{2}$$

wherein, $R^5$ represents a hydrogen atom, a hydrocarbon group having 4 to 30 carbons, or an organic group represented by $R^6$—(CO)—, $R^6$ represents a hydrocarbon group having 1 to 30 carbons, and "l" is an integer of $0 \leq l \leq 15$;

$R^2$ is a group represented by a general formula (3) —Y—O—X wherein, Y represents a divalent hydrocarbon group having 3 to 20 carbons and optionally containing at least one of an ether bond and an ester bond, and X represents a polyhydric alcohol-substituted hydrocarbon group having at least two hydroxyl groups and optionally contains alkoxy group or ester group;

$R^3$ is a monovalent branched type organosiloxane group represented by the following general formula (4), $$M_o M^R{}_p D_q D^R{}_r T_s T^R{}_t Q_u \tag{4}$$

wherein, $M=R^7{}_3 SiO_{0.5}$, $M^R=R^7{}_2 R^8 SiO_{0.5}$, $D=R^7{}_2 SiO$, $D^R=R^7 R^8 SiO$, $T=R^7 SiO_{1.5}$, $T^R=R^8 SiO_{1.5}$, $Q=SiO_2$, $R^7$ is an organic group of the same kind or different kinds selected from an alkyl group, an aryl group, an aralkyl group and a fluorine-substituted alkyl group having 1 to 30 carbons, and $R^8$ is an organic group represented by $-C_n H_{2n}-$; "n" represents an integer of $1 \leq n \leq 5$, "o" is an integer of 1 or larger, "q" and "s" each represents an integer of 0 or larger, "p", "r", "t", and "u" each represents 0 or 1; with the proviso that "s", "t" and "u" are not 0 simultaneously, a sum total of "p", "r" and "t" is 1, and when q=0, "o" represents 2 or larger and a sum total of "s" and "u" is 1 or larger;

$R^4$ is a monovalent organosiloxane group represented by the following general formula (5) or general formula (6), $$MM^R D_{v1} \tag{5}$$

$$M_w D_{v1} D^R{}_{v2} T^R{}_{v3} \tag{6}$$

wherein, M, $M^R$, D, $D^R$ and $T^R$ are the same as those described above; v1 is $0 \leq v1 \leq 1500$, v2 and v3 each represents the number of 0 or 1; with the proviso that a sum total of v2 and v3 is 1, and v1 and v3 are not 1 or larger simultaneously; W represents an integer of 2 to 3.

2. The silicone compound according to claim 1, wherein the silicone compound is represented by the following structural formula (1-1),

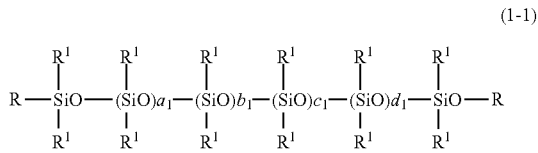

(1-1)

wherein, $R^1$, $R^2$, $R^3$, and $R^4$ are the same as those described above; R may be the same or different from each other and represents a group selected from $R^1$, $R^2$, $R^3$, and $R^4$; $a_1$ is the number in the range of 0 to 1000, $b_1$ is the number in the range of 0 to 200, $c_1$ is the number in the range of 0 to 200, and $d_1$ is the number in the range of 0 to 100; with the proviso that when $b_1=0$, at least one of Rs is $R^2$, and when c1=0, at least one of Rs is $R^3$.

3. The silicone compound according to claim 1, wherein, in the silicone compound, the "p" in the general formula (4) is p=1.

4. The silicone compound according to claim 2, wherein, in the silicone compound, the "p" in the general formula (4) is p=1.

5. A cosmetic comprising the silicone compound according to claim 1.

6. A cosmetic comprising the silicone compound according to claim 2.

7. A cosmetic comprising the silicone compound according to claim 3.

8. A cosmetic comprising the silicone compound according to claim 4.

* * * * *